(12) United States Patent
Visco

(10) Patent No.: US 10,512,578 B2
(45) Date of Patent: Dec. 24, 2019

(54) PATIENT STABILIZATION DEVICE AND METHODS OF USE

(71) Applicant: Anthony G. Visco, Chapel Hill, NC (US)

(72) Inventor: Anthony G. Visco, Chapel Hill, NC (US)

( * ) Notice: Subject to any disclaimer, the term of this patent is extended or adjusted under 35 U.S.C. 154(b) by 301 days.

(21) Appl. No.: 14/354,852

(22) PCT Filed: Apr. 24, 2014

(86) PCT No.: PCT/US2014/035286
§ 371 (c)(1),
(2) Date: Apr. 28, 2014

(87) PCT Pub. No.: WO2014/176418
PCT Pub. Date: Oct. 30, 2014

(65) Prior Publication Data
US 2015/0297435 A1    Oct. 22, 2015

Related U.S. Application Data

(60) Provisional application No. 61/815,345, filed on Apr. 24, 2013.

(51) Int. Cl.
| | |
|---|---|
| *A61G 13/12* | (2006.01) |
| *A61G 13/04* | (2006.01) |
| *A61G 13/10* | (2006.01) |
| *A61G 99/00* | (2006.01) |
| *A61F 5/37* | (2006.01) |

(Continued)

(52) U.S. Cl.
CPC .......... *A61G 13/123* (2013.01); *A61F 5/3776* (2013.01); *A61G 13/04* (2013.01); *A61G 13/101* (2013.01); *A61G 13/121* (2013.01); *A61G 13/122* (2013.01); *A61G 13/125* (2013.01); *A61G 13/1235* (2013.01); *A61G 13/1245* (2013.01); *A61G 99/00* (2013.01); *A61F 7/00* (2013.01); *A61F 2007/0022* (2013.01); *A61F 2007/0024* (2013.01); *A61F 2007/0027* (2013.01); *A61G 7/005* (2013.01); *A61G 7/0755* (2013.01); *A61G 2200/327* (2013.01); *A61G 2210/70* (2013.01); *A61G 2210/90* (2013.01)

(58) Field of Classification Search
CPC ........ A61G 7/08; A61G 7/104; A61G 13/126; A61G 13/1235; A61G 13/122; A61G 13/12; A61G 1/06; A47C 27/14
USPC .... 5/710, 713, 731, 603; 128/869, 870, 876, 128/846, 849
See application file for complete search history.

(56) References Cited

U.S. PATENT DOCUMENTS 3,156,500 A * 11/1964 Kerr ...................... A61G 15/125
297/230.13
4,620,337 A * 11/1986 Williams ........... A61G 7/05707
5/691

(Continued)

OTHER PUBLICATIONS

Supplementary European Search Report dated Aug. 15, 2016, from EP 14 78 7969.

(Continued)

*Primary Examiner* — Ophelia A Hawthorne
*Assistant Examiner* — Caitlin A Carreiro
(74) *Attorney, Agent, or Firm* — Stephen Kenny; Foley Hoag LLP

(57) ABSTRACT

Devices, systems and methods for patient stabilization are disclosed.

33 Claims, 25 Drawing Sheets

(51) Int. Cl.
*A61G 7/005* (2006.01)
*A61G 7/075* (2006.01)
*A61F 7/00* (2006.01)

(56) References Cited

U.S. PATENT DOCUMENTS

| | | | | |
|---|---|---|---|---|
| 5,549,121 | A * | 8/1996 | Vinci | A61F 5/3776 |
| | | | | 128/878 |
| 5,742,963 | A * | 4/1998 | Trevino | A61G 1/00 |
| | | | | 128/845 |
| 5,785,716 | A * | 7/1998 | Bayron | A61F 7/00 |
| | | | | 126/204 |
| 6,227,201 | B1 * | 5/2001 | Ferko, III | A61G 1/01 |
| | | | | 128/869 |
| 8,156,941 | B1 * | 4/2012 | Simms | A47C 20/021 |
| | | | | 128/845 |
| 2008/0178390 | A1 * | 7/2008 | DuDonis | A47C 20/021 |
| | | | | 5/632 |
| 2010/0275377 | A1 | 11/2010 | West | |
| 2011/0047706 | A1 | 3/2011 | Hiebert | |
| 2011/0296609 | A1 | 12/2011 | Giap | |
| 2013/0174853 | A1 * | 7/2013 | Pigazzi | A61G 13/122 |
| | | | | 128/845 |
| 2013/0312189 | A1 * | 11/2013 | Sarma | A61G 13/122 |
| | | | | 5/621 |

OTHER PUBLICATIONS

International Search Report from related international application PCT/US2014/035286, dated Apr. 2, 2015.

\* cited by examiner

PATIENT STABILIZATION DEVICE AND METHODS OF USE

RELATED APPLICATIONS

This application is the U.S. national phase of International Patent Application No. PCT/US2014/035286, filed Apr. 24, 2014, which claims priority to and benefit of U.S. Provisional Application Ser. No. 61/815,345 filed 24 Apr. 2013, which is hereby incorporated herein by reference in its entirety.

FIELD OF THE INVENTION

The present disclosure relates to the field of surgery, and more particularly to a device, and methods of using such a device, to position and/or stabilize a patient during a surgical procedure.

BACKGROUND

To help facilitate both laparoscopic and robotic surgery for urologic, gynecologic and other general surgical procedures, a patient is often positioned on an operating room ("OR") table with the head tilted down (generally referred to as the Trendelenburg position). There are many current stabilization options available today to help position a patient in such a position, but all options have shortcomings. For example, one such option is based on a reusable "bean bag" device. The device consists of an enclosed airtight vinyl pouch filled with beads. The patient is encased in the floppy bean bag, and then suction is applied to the bean bag to remove air, resulting in a very firm cocoon-like enclosure which is then taped to the surgical table. Such reusable devices carry an increased risk of patient infection since the patient's skin in direct contact with the reused vinyl surface. Moreover, any repositioning requires significant delay. In order to adjust one side of the bean bag air is released to the entire bean bag requiring effort to maintain the patient position.

Another reusable device includes a gel pad that is placed under the patient. Such devices face similar problems, such as increased risk of infection because the patient's skin is in direct contact with the pad and the device requires additional work/time, including the need to warm the gel pad prior to patient contact.

Yet another option is based on a foam egg crate positioned between the patient and the operating room table mattress, where the foam egg crate is taped to the operating table. If the foam is cut to generally the size of the bed, taping is relatively straightforward, however, this configuration does not adequately address positioning of the arms and hands. If a wide piece of foam were to be utilized, this would require 4-6 holes to be made in the foam to allow wide pieces of tape to run from the bed on one side, through a hole, across the foam to the other side, through the contralateral hole, and then to the OR table. Such a design requires additional time and effort.

Whether the gel pad, "bean bag" or the foam egg crate method are used, the arms of the patient are wrapped with separate pieces of foam and then tucked with additional and separate foam using a large sheet, such as a bed sheet. Often the hands extend beyond the base of the table and require separate wrapping to protect them during the surgical procedure. Additional foam is then placed across the chest and the upper torso is secured to the bed using wide tape or seatbelt-like straps, often including a hook and loop fastener, such as Velcro™. However, this set up often still results in patient slippage. Mattress pads typically include a hook and loop fastener on their back side to secure the pad to the OR table; use of a bed sheet as described interferes with that fastener and makes the mattress pad difficult to secure to the table.

Moreover, all of the above-mentioned devices also commonly use adhesive tape, typically of paper or silk. The roll of tape is multi-use and represents an infectious disease risk because the edges of the tape are sticky and the roll is maintained in the operating room (OR) between patients.

Hence, there is a need for an improved device that provides easier, faster and more secure patient positioning, improved infection control, improved protection of the patient's upper extremities during laparoscopic and robotic surgery, and less waste compared to current options.

SUMMARY

Devices, systems and methods for patient stabilization are disclosed.

DETAILED DESCRIPTION

Figure 1:
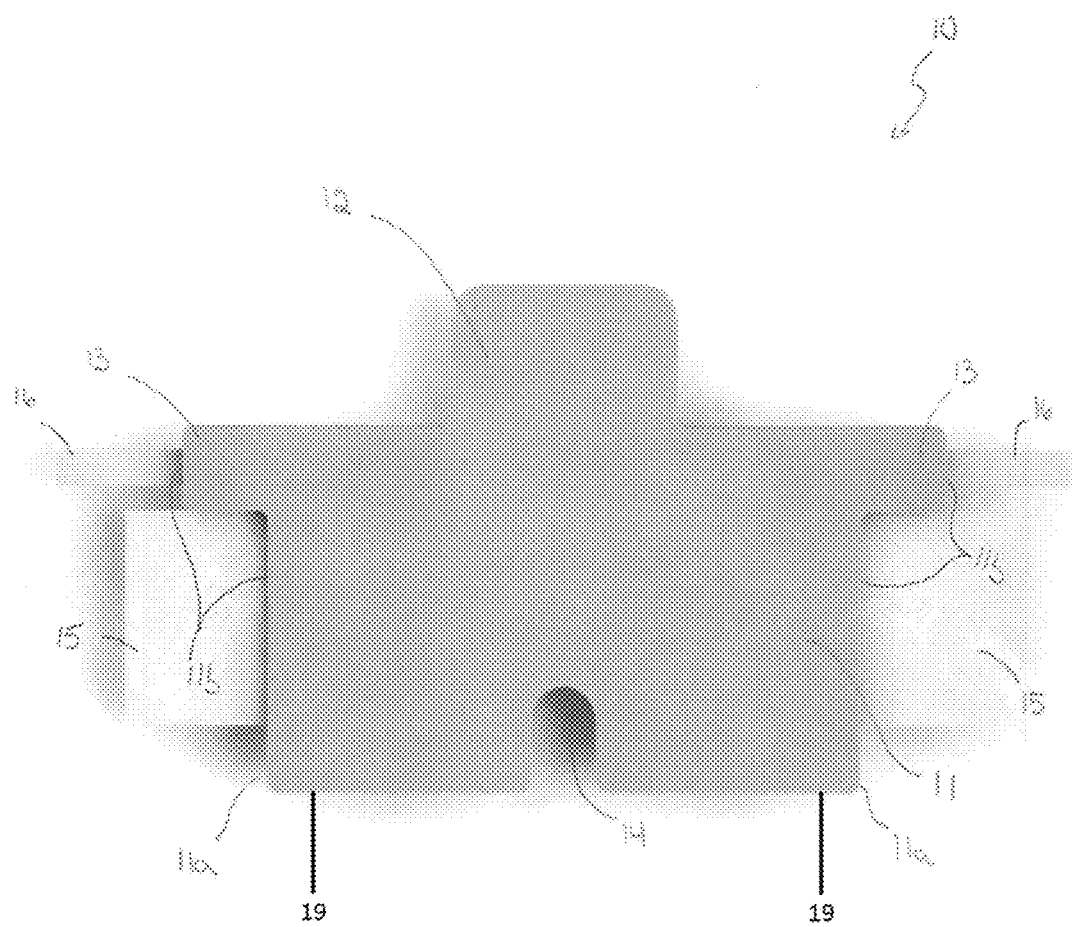
FIG. 1 is a top view of a patient stabilizing device according to one embodiment of the present disclosure.

The present disclosure addresses the previously mentioned shortcomings. In some embodiments, a stabilization device can be an all in one disposable base with a custom design to allow for patient stability and the tucking of the arms to protect the patient's upper extremities. Other embodiments are a kit of multiple parts. Other embodiments include a method of using such devices or kits.

One aspect of the present disclosure provides a patient stabilization device including a supporting material having a generally rectangular body portion, a head portion, and two transversely disposed side arm wings. The device can include a cut out portion on the inferior (foot) side, a sturdy fabric comprising affixed to at least a portion on the back side of the supporting material, and at least one fastener located on the back side of the device to secure the device to the operating table bed.

In some embodiments, the supporting material includes the general size and shape of the operating room table/bed. In other embodiments, the supporting material includes an inferior portion (i.e., towards the patient's feet) that extends beyond the edge of the table. In some embodiments, rectangular body portion extends at least 1", 2", 3", 4", 5", 6", 7", 8", 9", 10", 11", or 12" beyond the inferior (i.e., towards the patient's feet) edge of the table. In certain embodiments, the rectangular body portion extends between 5" and 6" from the inferior edge of the table. In other embodiments, the rectangular body portion extends at least 1", 2", 3", 4", 5", 6", 7", 8", 9", 10", 11", 12", 13", 14", 15", 16", 17", 18", 19", or 20" beyond the lateral edges of the table. In certain embodiments, the rectangular body portion extends between 9" and 13" beyond the lateral edge of the table. In yet other embodiments, the device may be made larger to fit those tables and/or patients that are larger than normal (e.g., obese patients, unusually tall patients, etc.).

In some embodiments, the support material is selected from the group consisting of one or more spring assemblies, foams, gel pads. In some embodiments, the foam is selected from the group consisting of polyurethane, silicone, vinyl, nylon, polyethylene vinyl acetate (PEVA), and the like. In other embodiments, the support material includes a plurality of pods or chambers that are filled with an incompressible fluid such as water, viscous oil, or some other biocompatible fluid. In yet other embodiments, the pods or chambers are filled with a gas (e.g., air, nitrogen, etc.). Yet in other embodiments the pods or chambers are filled with a fluid, gas or combination thereof. In yet other embodiments, the support material may be filled with a material that can be heated or cooled to help regulate the body temperature of the patient or to specifically heat or cool certain body parts or organs.

In some embodiments, the supporting material can have a thickness of at least 0.25", 0.5", 0.75", 1", 2", 3", 4", 5", 6", 7", 8", 9", 10", 11", and 12". In certain embodiments, the support material includes a thickness between 0.5" and 6".

In some embodiments, the back surface of the support material can include a slip-resistant material. In some embodiments, the slip-resistant material is selected from the group consisting of rubber, adhesive tapes and glues, anti-skid materials, fastener/interlocking materials, e.g., hook and loop fasteners, or any other material that tends to increase the friction between the device and the under lying OR table, or mattress, or whatever surface the device is deployed upon.

In some embodiments, the stabilizing device further includes a custom cut out. In some embodiments, the cut out includes a U-shape. In other embodiments, the cut out is at least 1", 2", 3", 4", 5", 6", 7", 8", 9", 10", 11", 12" deeper than the standard cut out of an operating room table.

In some embodiments, the stabilizing device can include an infection control barrier material that covers the sides and the base of the table to isolate the patient from the OR table and mattress, and the table and mattress from bodily fluids. In some embodiments, the material is transparent. The material could be plastic, or a nonwoven, material, etc.

In some embodiments, the back surface of the device can include a sturdy fabric that is affixed at least to the arm wings and/or the rectangular body portion. In some embodiments, the sturdy fabric is affixed to the entire back side of the device. In certain embodiments, the sturdy fabric is selected from the group consisting of nylon, rubber, flexible plastic and the like. In other embodiments, the fabric is secured using a fastening means positioned between the patient's body and arm. In some embodiments, the fastening means is selected from the group consisting of latches, snaps, ties, etc. instead of with the patient's body weight.

In some embodiments, the side wings can include a sturdy fabric. In some embodiments, the sturdy fabric is selected from the group consisting of nonwoven materials, nylon, rubber, flexible plastic and the like. In other embodiments, the sturdy fabric attached to the side wings further includes a fastening means. In some embodiments, the fastening means is selected from the group consisting of latches, snaps, ties, etc.

In some embodiments, the stabilizing device can include at least one fastener means positioned on the backside of the device to secure it to the operating room table. In some embodiments, the device can include at least 2 or 3 fastener means. In some embodiments, the fasteners are positioned at the head portion of the device, the rectangular body portion of the device, the inferior (i.e. foot end) of the device, or combinations thereof. In some embodiments, the fastener means secures the device by fastening to the rails of the operating room table. In other embodiments, the fastener means also help secure the operating room table mattress to the bed. In some embodiments, the fastening means is selected from the group consisting of ties, hook and loop fasteners, adhesive strips, snaps and the like.

In some embodiments, the stabilizing device can include an additional piece of support material and a fastening means to secure the patient's upper chest to the operating room table.

Another aspect of the present disclosure provides a method of stabilizing a patient during a medical procedure that occurs while the patient is supported on an operating table, and wherein the patient is in the Trendelenburg position, supine upon a patient stabilizing device. Such methods can include fastening the device to the operating table; positioning the patient on the device; pulling on the sturdy fabric attached to the side arm wings thereby rolling the side arm wings upwards and inwards to wrap the patient's arms; pulling on the sturdy fabric that is affixed to the back side of the device thereby securely wrapping the arms; tucking the fabric under the patient or fastening the fabric to the device; and ensuring all fasteners are attached.

Another aspect of the present disclosure provides all that is illustrated and described herein.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

FIG. 1 is a top view of one embodiment of a patient stabilizing device 10 in its unfurled and spread out configuration. The device is made of a supporting material and includes a generally rectangular body portion 11 having an inferior end 11a and lateral edges 11b, a head portion 12, and two transversely disposed side chest wings 13. The rectangular body portion 11 is generally wider than the operating room table and includes an inferior portion 11a (i.e., towards the patient's feet) that extends beyond the edge of the table. The rectangular body portion 11 may extend at least 1", 2", 3", 4", 5", 6", 7", 8", 9", 10", 11", or 12" beyond the inferior edge (i.e., towards the patient's feet) of the table. In some embodiments, the rectangular body portion extends between 5" and 6" from beyond the inferior edge of the table. It is also within the scope of the present disclosure that the device may be made larger to fit those tables and/or patients that are larger than normal (e.g., bariatric patients, abnormally tall patients, etc.). In such embodiments, the general shape is maintained, however, the overall size is adjusted to fit the patient and/or table. The lateral edges 11b and side chest wings 13 preferably extend widely beyond the edges of the table and are made of a contiguous support material that allows for easy wrapping of the upper extremities. In some embodiments, the lateral edges of the rectangular body portion extends at least 1", 2", 3", 4", 5", 6", 7", 8", 9", 10", 11", 12", 13", 14", 15", 16", 17", 18", 19", or 20" beyond the lateral edges of the table. In certain embodiments, the lateral edges of the rectangular body portion extends between 9" and 13" beyond the lateral edge of the table. The right and left lateral portions of the body portion 11 are sometimes referred to herein as right and left arm wings 19, although generally the arm wings and the body portions will be connected and in some cases, integrally formed (explained in more detail with reference to FIGS. 15-19).

In some embodiments, the lateral edges of the rectangular body, or left and right arm wings 19 as the case may be, can be designed to allow for folding in an inward manner only (e.g., only towards the patient, and not down toward the floor). Folding inward, the arm wings 19 can wrap around the patient's arms; unfolded, the arm wings 19 can extend out to the sides and support the weight of the patient's arms. The ability to fold in one direction and not the other can be achieved by attaching a support material to the bottom of the arm wings 19. Without such support, the later portions of the rectangular body, or arm wings 19, can sag downward due to gravity since they extend beyond the lateral edge of the OR table. It is within the scope of the present disclosure that additional support may be added to allow the support material to be folded inward, but prevent sagging. For example, segmented connector strips may be placed on the back surface running 90 degrees to the long axis of the patient. Alternatively, weaving, suture material or other reinforcing material strips may be placed on the top/front portion of the device to resist posterior folding (i.e., sagging) of the lateral edges, but would not prevent forward flexion. In such embodiments, there would no longer be any need to attach arm boards to support the patient's arm while an IV catheter is placed and the patient is placed under general anesthesia prior to fully securing the patient to the device.

The stabilizing device 10 is largely made of a support material, for example any material that is capable of supporting the weight of the patient without bottoming out and allowing for the device to be conformed (e.g., wrapped) around the patient. Examples include one or more spring assemblies, where the spring assemblies may utilize various spring types such as leaf or compression springs or various other types of biasing mechanisms, foams such as polyurethane, silicone, vinyl, nylon, polyethylene vinyl acetate (PEVA), and the like, and gel pads. In some embodiments, the support material may include a plurality of pods or chambers that are filled with an incompressible fluid such as water, viscous oil, or some other biocompatible fluid. In other variations, the pods or chambers may filled with a gas such as air, nitrogen, etc. In some embodiments the pods or chambers may be filled with a fluid, gas or combination of both depending on the desired degree of cushioning and force distribution. In yet other embodiments, the support material may be filled with a material that can be heated or cooled to help regulate the body temperature of the patient (e.g., lower, raise or maintain the body temperature of the patient) or to heat or cool certain body parts or organs.

The thickness of the supporting material is such that it provides adequate support for the patient but also does not interfere with the healthcare provider. Suitable thicknesses may be at least 0.25", 0.5", 0.75", 1", 2", 3", 4", 5", 6", 7", 8", 9", 10", 11", and 12". In some embodiments, the support material includes a thickness between 0.5" and 6".

The back surface of the support material, or the back surface of the entire device, can include a slip-resistant material, for example, any biocompatible material that provides friction to help keep the patient in one place when the operating room table is inverted. Such materials include, but are not limited to, rubber, silicone, adhesive tapes and glues, anti-skid materials, fastener/interlocking materials such as Velcro™, and the like.

Figure 2:
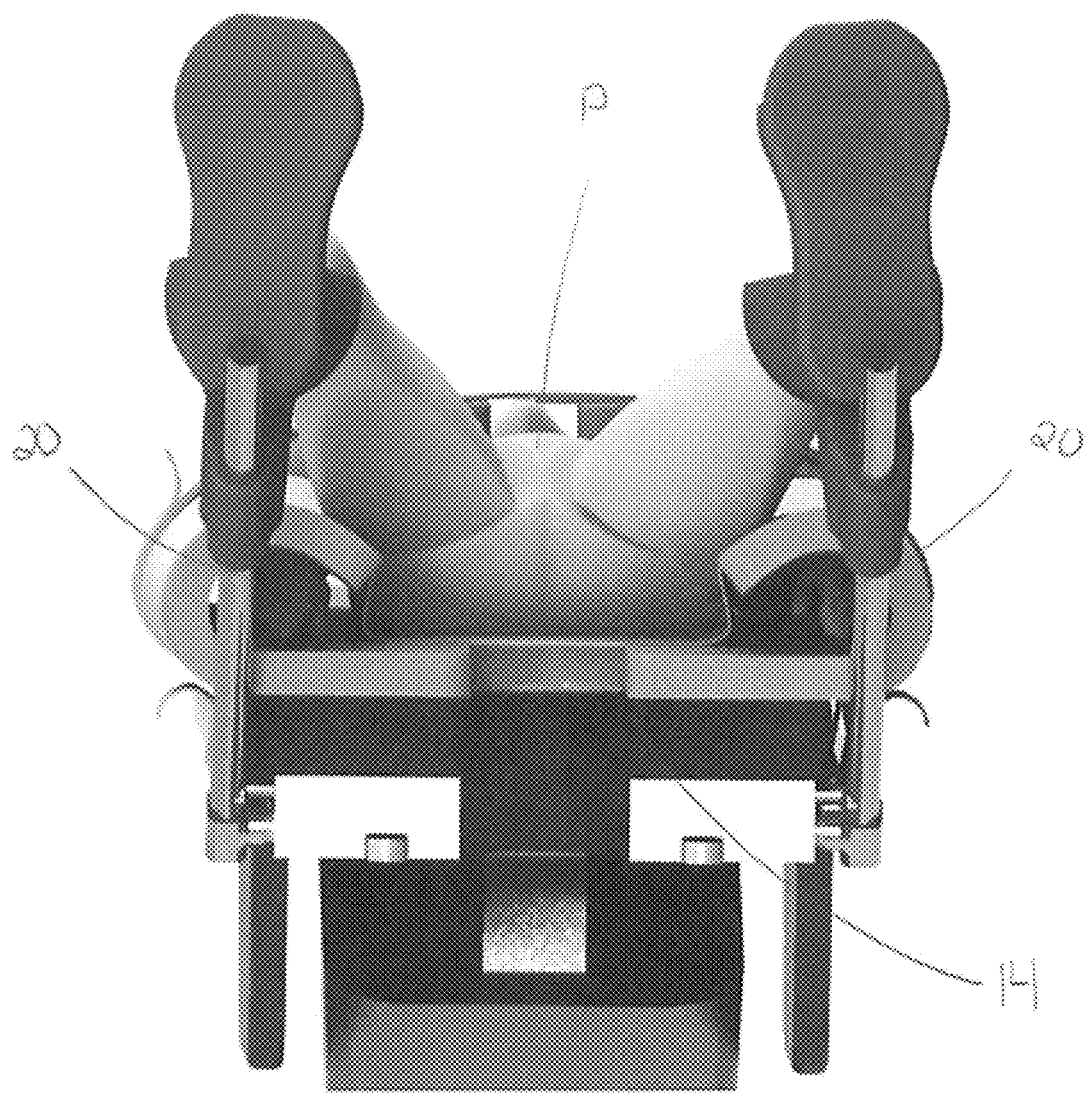
FIG. 2 is an inferior view of the same patient stabilizing device showing access to the perineum of a patient according to one embodiment of the present disclosure.
Figure 3:
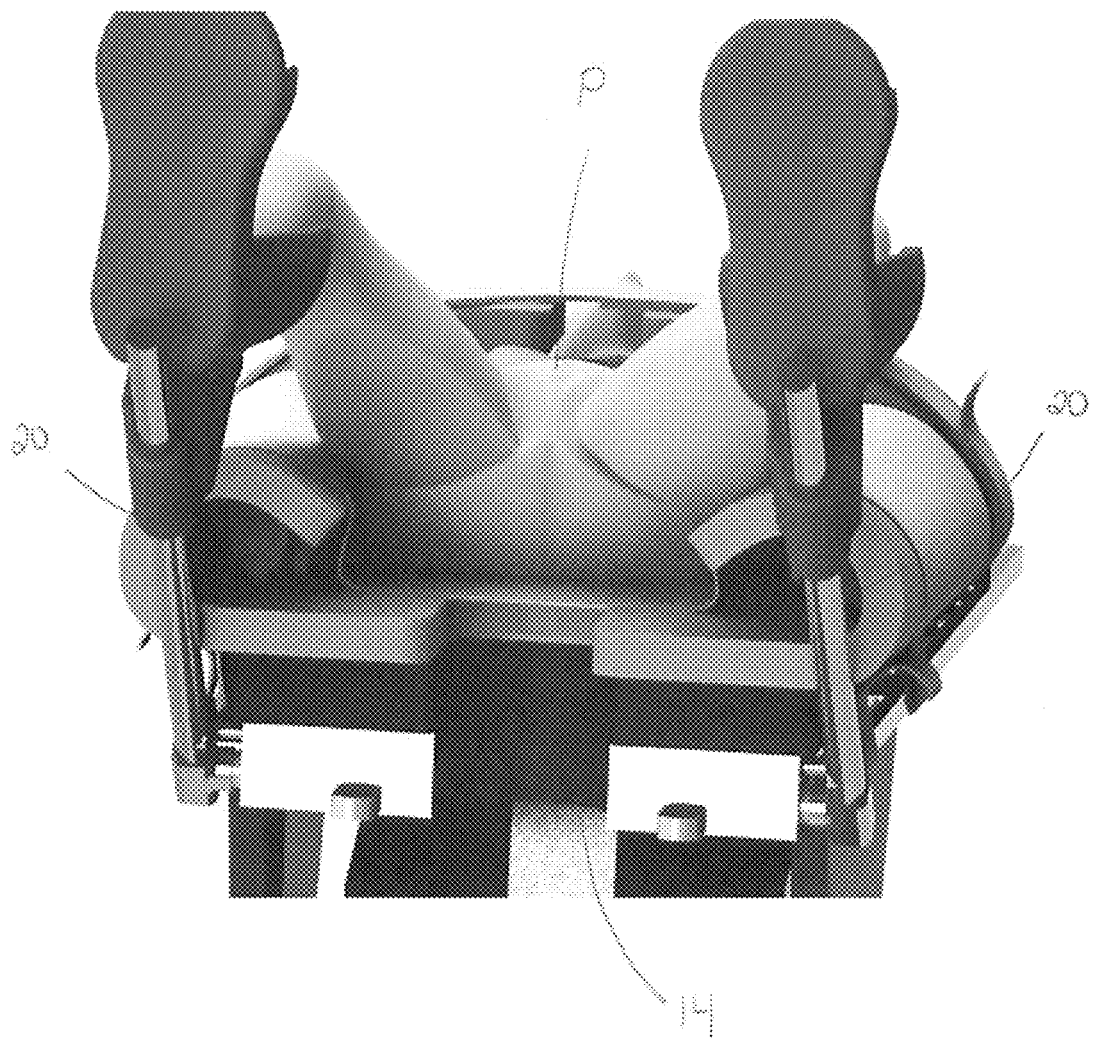
FIG. 3 is a close-up inferior view of the same patient stabilizing device showing access to the perineum of a patient according to one embodiment of the present disclosure.

Referring again to FIG. 1, the device is shown with a notch 14 to allow access to the perineum and configured in a manner to facilitate adequate protection of the patient's hand. FIGS. 2 and 3 show inferior views of the device with a patient stabilized by device. The notch 14 allows the health care provider easy access to the perineum of the patient P and also allows for adequate wrapping of the patient's hands. The notch 14 can be of any shape to facilitate access of the health provider to the perineum of the patient. As shown the notch defines a U-shape. The cut out can be at least 1", 2", 3", 4", 5", 6", 7", 8", 9", 10", 11", 12" deeper than the standard cut out of an operating room table, thereby allowing the device to be fixed to the bed such that the device itself extends beyond the end of the bed by at least 1", 2", 3", 4", 5", 6", 7", 8", 9", 10", 11", 12". This feature allows both the arms and the hands of the patient to be simultaneously wrapped during the tucking process. Typically, a patient's hands, when at their side, extend beyond their buttocks and hips. Hence, when a patient is positioned on the operating table, their pelvis is generally at the bottom edge of the table and therefore the hands extend unsecured beyond the edge of the bed. Exposed hands are at risk of compression and/or injury during movement of the operating table and during the surgical procedure. Separately wrapping the hands with foam or similar material requires additional foam and significant time. This deep notch 14 corrects the problem by extending the material beyond the hands, allows for wrapping of the hands simultaneously and efficiently with the wrapping of the arms while avoiding interference with access to the perineum.

Such stabilizing devices can also include an infection control barrier (not shown) that covers the sides and the base of the table to prevent transfer of bodily fluids to the OR table and protects the patient from any residual infectious material or residual bodily fluids. The barrier be made of a wide variety of materials, such as plastic, cellophane, non-woven material, cloth and the like that can prevent the spread of infection from bodily fluids released during a surgical procedure. In some embodiments, the barrier material is transparent, such as clear plastic. Such infection prevention can be especially important in the case of surgery at or near the perineum, as the perineum is often highly contaminated with bacteria, bodily fluids, urine and bowel content. Thus is can be particularly useful to keep the underlying OR table isolated from such contaminants.

Figure 4:
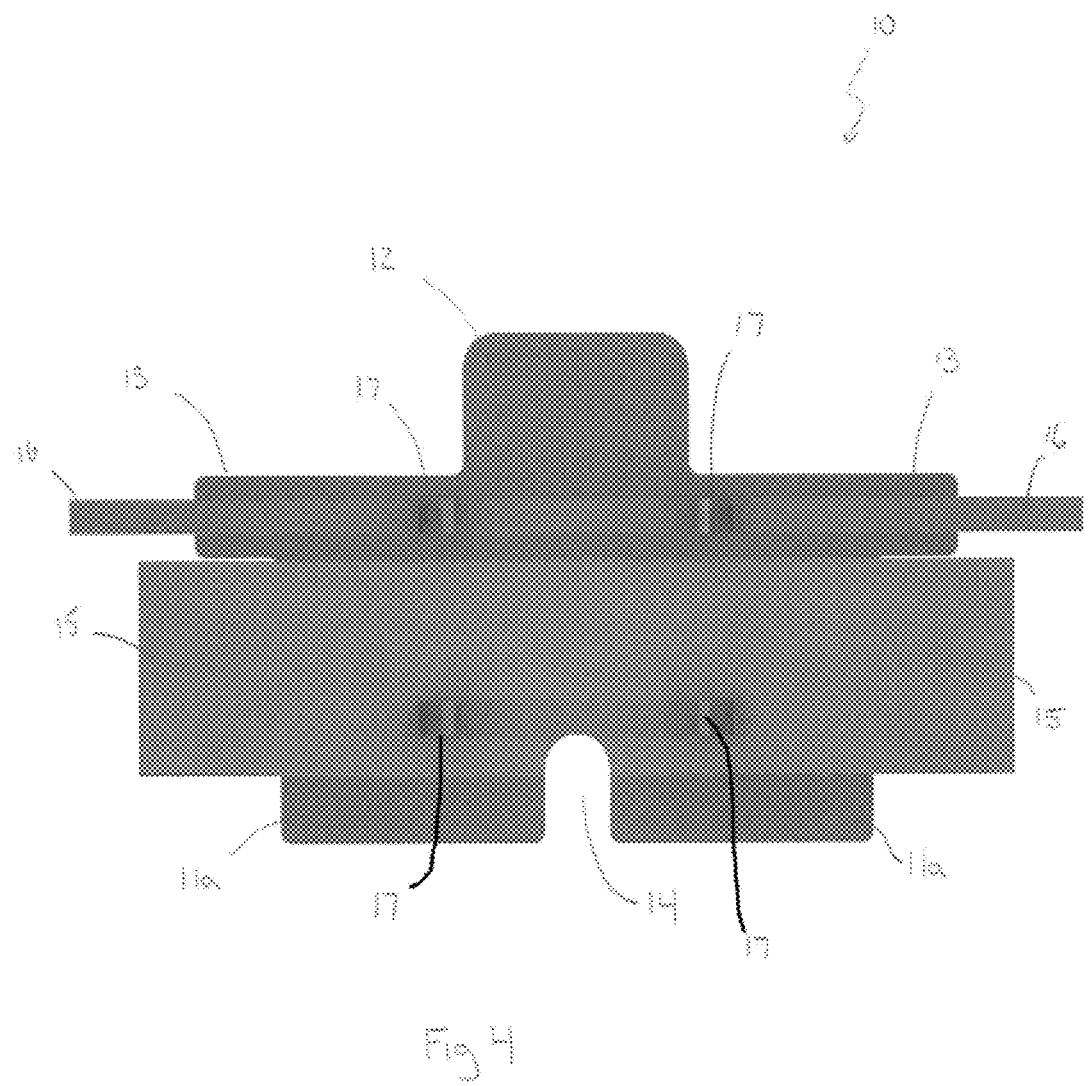
FIG. 4 is a view of the backside of the same patient stabilization device according to one embodiment of the present disclosure.
Figure 5:
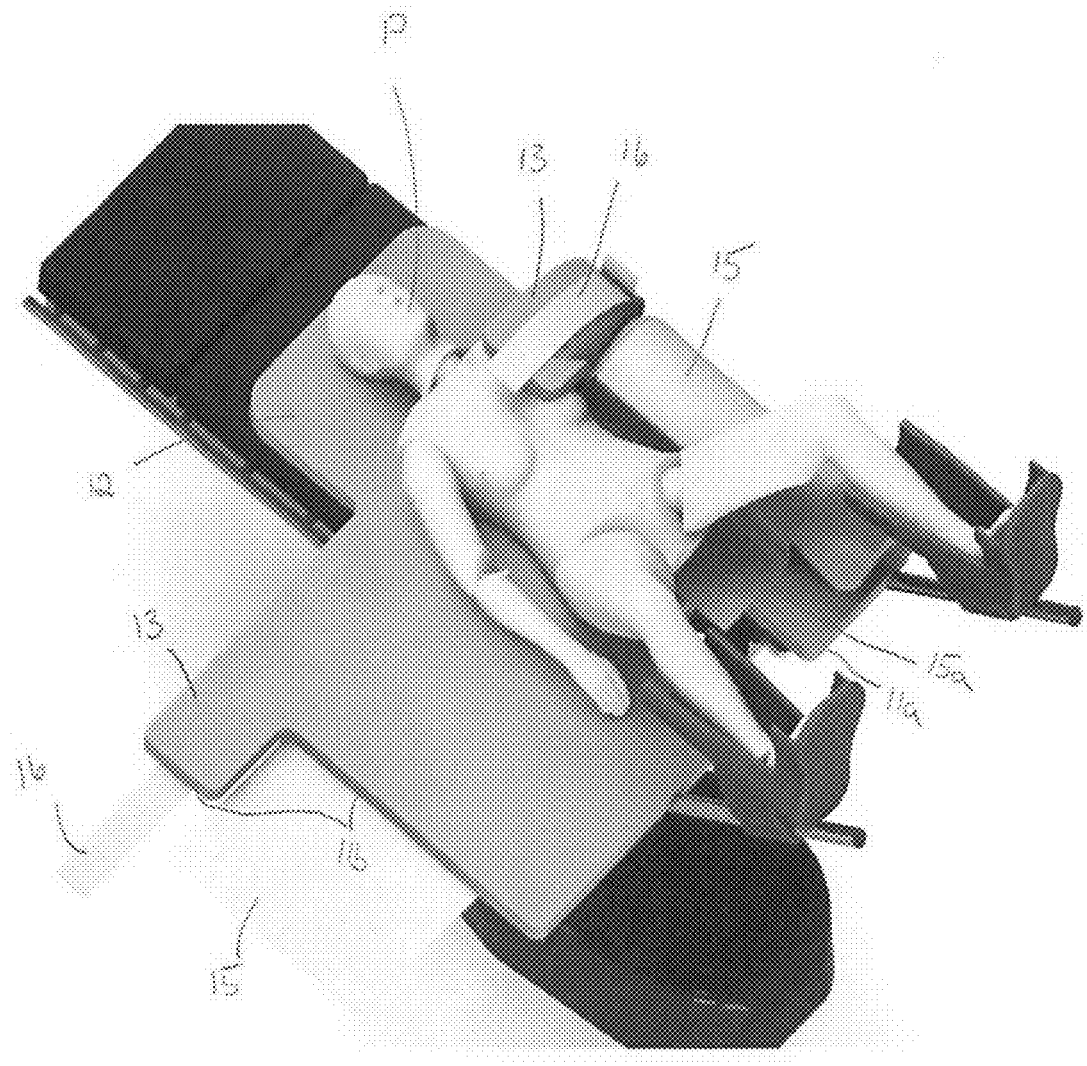
FIG. 5 is a top view of the same patient stabilization device showing how the device secures the arm of a patient according to one embodiment of the present disclosure.
Figure 6:
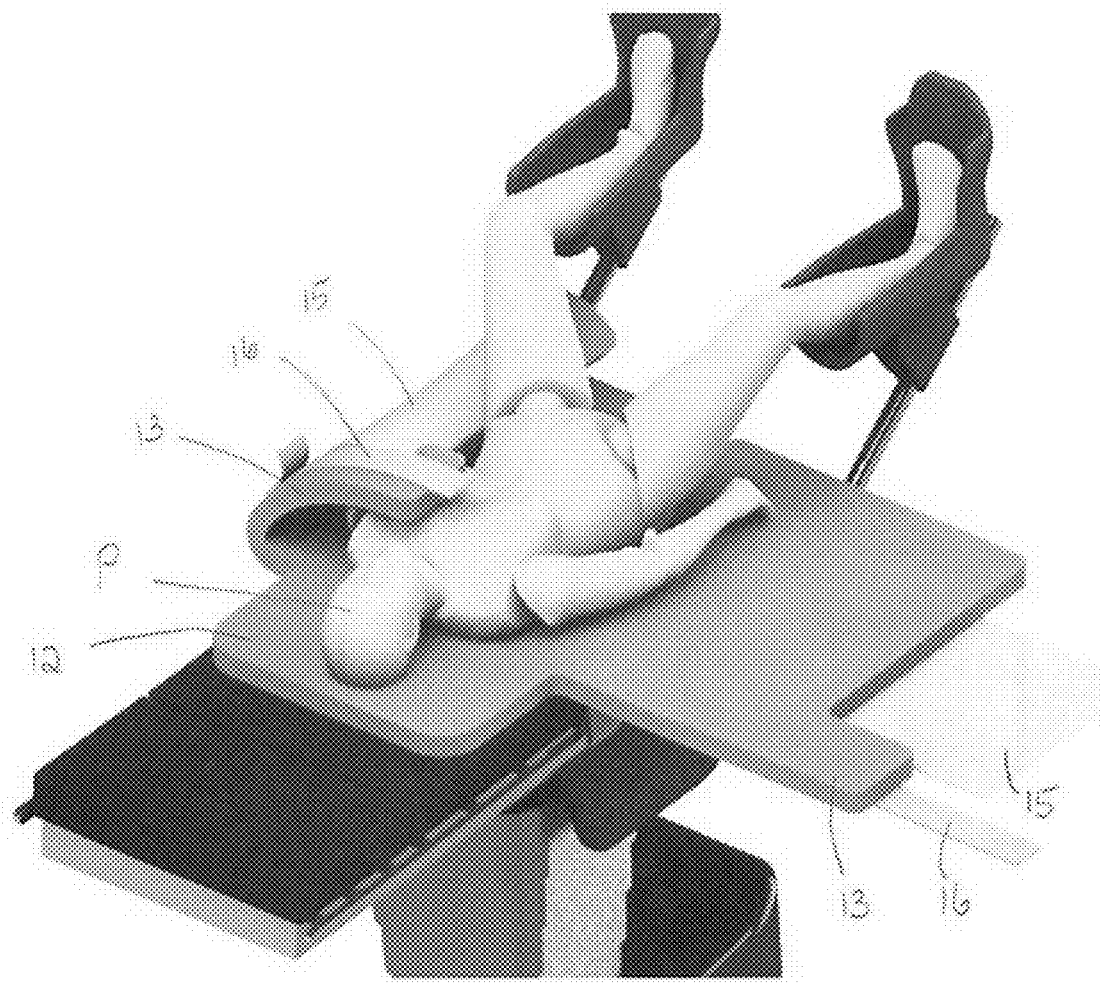
FIG. 6 is another top view of the same patient stabilization device showing how the device secures the arm of a patient according to one embodiment of the present disclosure.
Figure 7:
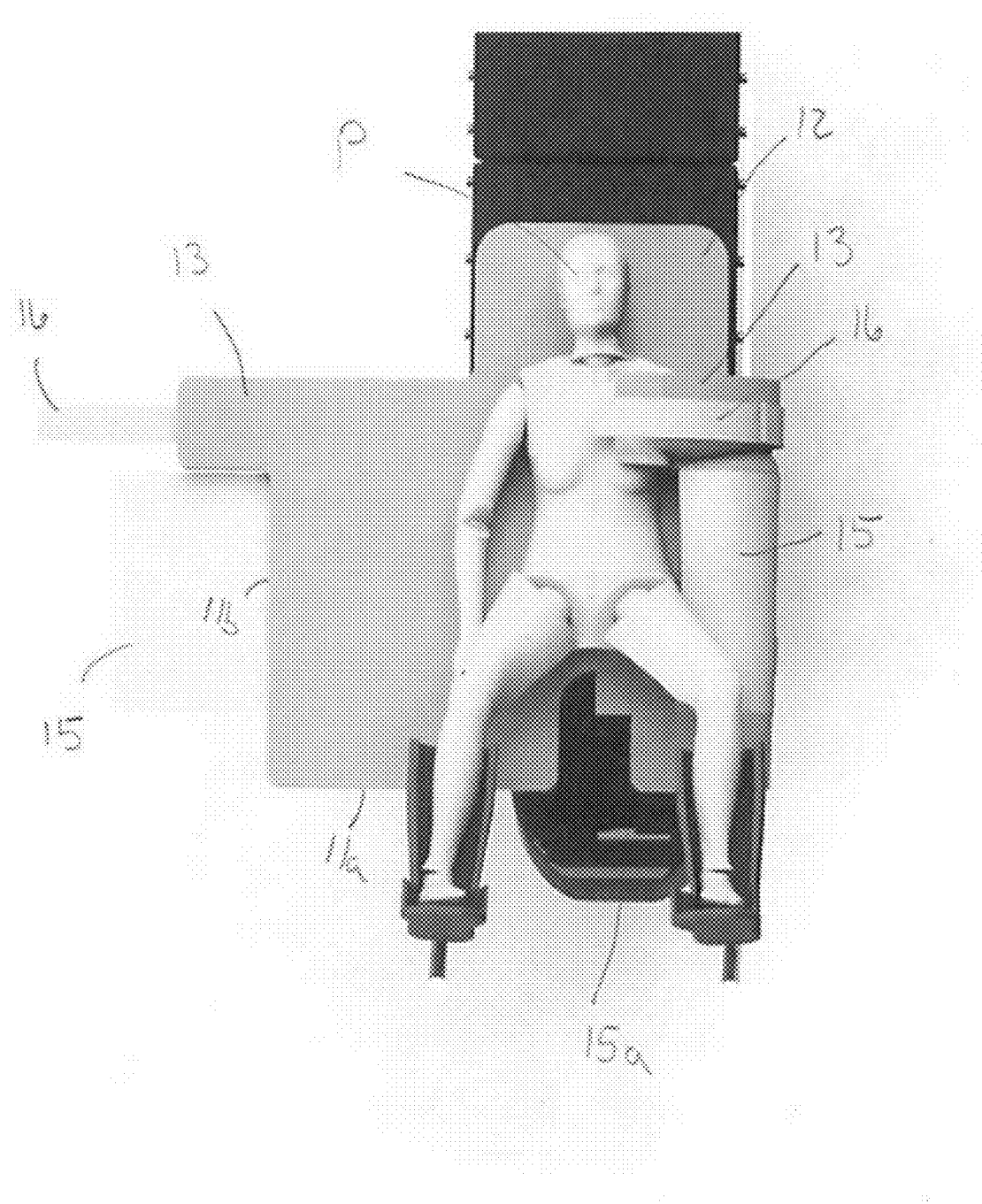
FIG. 7 is yet another top view of the same patient stabilization device showing how the device secures the arm of a patient according to one embodiment of the present disclosure.
Figure 8:
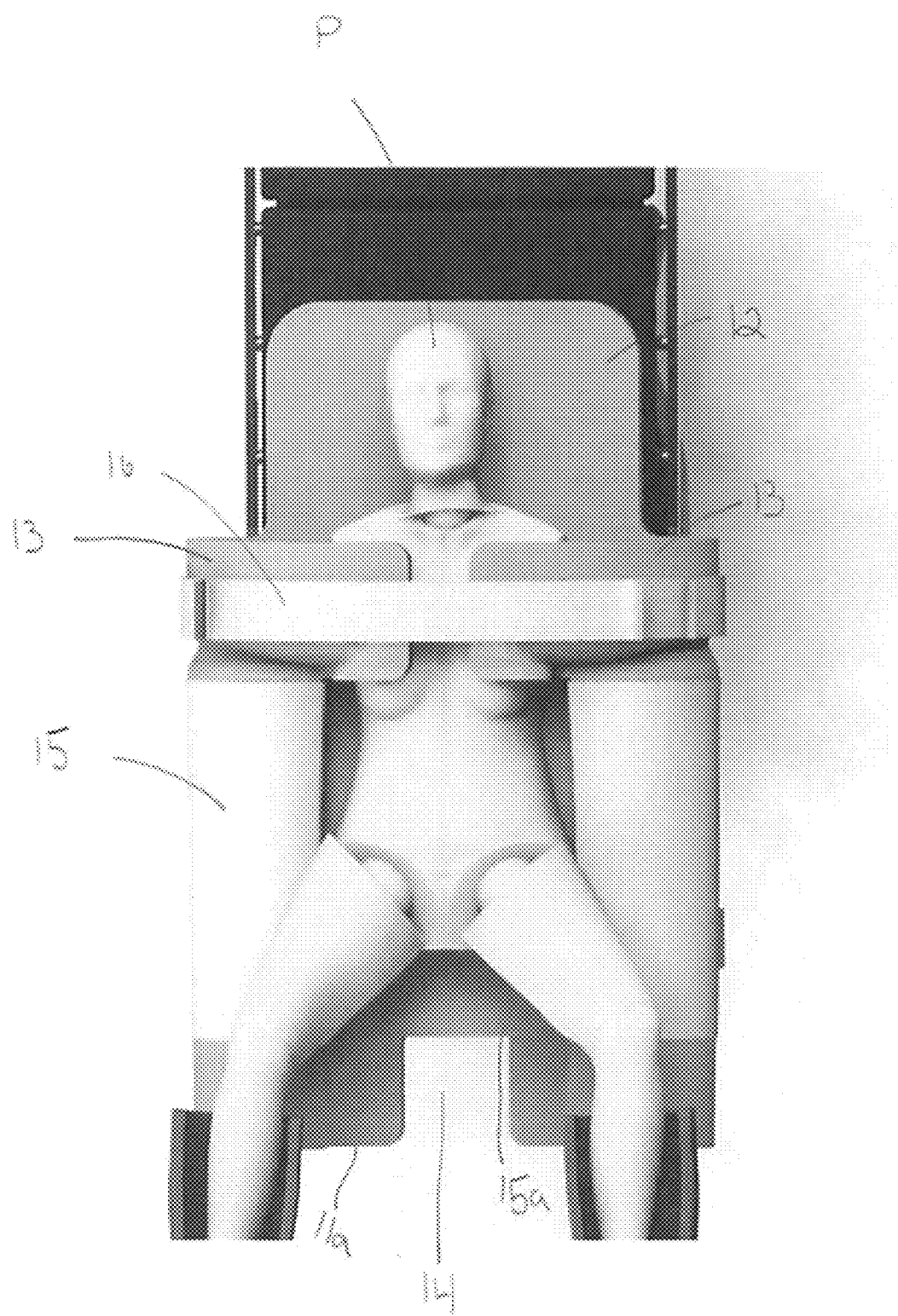
FIG. 8 is a top view of the same patient stabilization device showing the patient completely secured according to one embodiment of the present disclosure.

Referring now to FIG. 4, the bottom surface of the device, i.e., the surface of the device intended to contact the OR table, can also include a sturdy fabric sheet 15 that can be affixed to the arm wings 19 and/or to other parts of the rectangular body portion 11. In some embodiments, the sturdy fabric is affixed to the entire back side of the device. In other embodiments, the sturdy fabric is attached to the arm wings 19. The fabric sheet 15 can be a single sheet as shown in FIG. 4, or can be configures as two separate sheets, one attached to each arm wing 19. The sheet 15 may include any biocompatible fabric that resists tearing, such as non-woven materials, nylon, rubber, flexible plastic and the like. In use, and as shown in FIGS. 5-7, the fabric securely wraps the arms and then is tucked under the back of the supine patient P, thereby using the patient's weight to hold the arms in a tucked position at the patient's side. In some embodiments, the fabric may be secured using fasteners, latches, snaps, ties, etc. instead of with the patient's body weight. In such embodiments, the fabric would be secured by an appropriate mechanism, e.g., hook and loop fastener, snap, tie, latch, etc., located on the front portion of the device, between the patient's body and arm. In some embodiments, the sheet 15 is held in place only by the weight of the patient P, and the sheet includes no fasteners at all.

The chest wings 13 that extend beyond the edges of the operating room table can be made of the same material as the body portion 11. The chest wings 13 can also include a sturdy fabric or strap 16. As shown in FIGS. 5-7, the strap 16 allows the support material to roll upwards and inwards to wrap the patient's arms, however, in some embodiments the strap 16 will not allow the support material to flex posteriorly or downward similar to the arm wings 19 described above. This feature obviates the need for arm boards, saving both time and space. The strap 16 may include any biocompatible fabric that resists tearing, such as nonwoven materials, nylon, rubber, flexible plastic and the like. The strap 16 also can include a fastening means (not shown) that allows for the strap 16 to be fastened and secured once rolled upwards and inwards. The fastening means is preferably easy to operate and quick to fasten/unfasten. Such fastening means may include, but are not limited to, ties, hook and loop fasteners, adhesive strips, snaps, and the like. An added benefit of such an embodiment provides for the ability to gently wrap the patient in the device around the chest while he/she is going to sleep, before securely wrapping the arms. This provides comfort and helps to maintain body temperature. The chest wings 13 can be brought over the patient but their arms are not tucked as, generally, the patient needs to be moved down in the bed prior to tucking the arms. It is solely at that point to wrap the patient for comfort and warmth but the fastening means holds the patient in place for safety. Without such a fastening means, a separate fastening means or other safety strap is necessary to prevent the patient from falling off the bed while he/she is going off to sleep.

Referring again to FIG. 4, the stabilizing device can also include at least one fastener 17 positioned on the back side of the device to secure it to the operating room table. Preferably, the device includes at least 2 or 3 fasteners on each lateral side. The fasteners can be positioned at the head portion of the device, the rectangular body portion of the device, the inferior (i.e. foot end) of the device, or combinations thereof. In some embodiments, the fasteners secure the device by fastening to the rails of the operating room table. In other embodiments, the fasteners also help secure the operating room table mattress to the bed. The fasteners are preferably easy to operate and quick to fasten and unfasten. Such fastening means may include, but are not limited to, ties, hook and loop fasteners, adhesive strips, snaps and the like.

As shown in FIG. 4, the fasteners are fixedly attached to the bottom side of the device 10. As one alternative, fasteners can be separate straps that run along the front of the device and are configured to pass through holes in the device to secure the device to the rails of the operating table and when securely fastened serve to also secure the mattress to the operating table 10. This embodiment is explained in more detail with reference to FIG. 19 below.

In some embodiments, the stabilizing device can include an additional piece of support material and a fastening means to secure the patient's upper chest to the operating room table (not shown).

Another aspect of the present disclosure provides a method of stabilizing a patient during a medical procedure that occurs while the patient is supported on an operating table, and wherein the patient is in the Trendelenburg position, comprising, consisting of, or consisting essentially of providing a stabilizing device provided herein; fastening the device to the operating table using the fastening means; positioning the patient on the device, wherein the patients head is positioned at the head portion of the device; pulling on the sturdy fabric attached to the side wings thereby rolling the side wings upwards and inwards to wrap the patient's arms; pulling on the sturdy fabric that is affixed to the entire back side of the device thereby securely wrapping the arms; tucking the fabric under the patient or fastening the fabric to the device; and ensuring all fasteners are attached.

Figure 9:
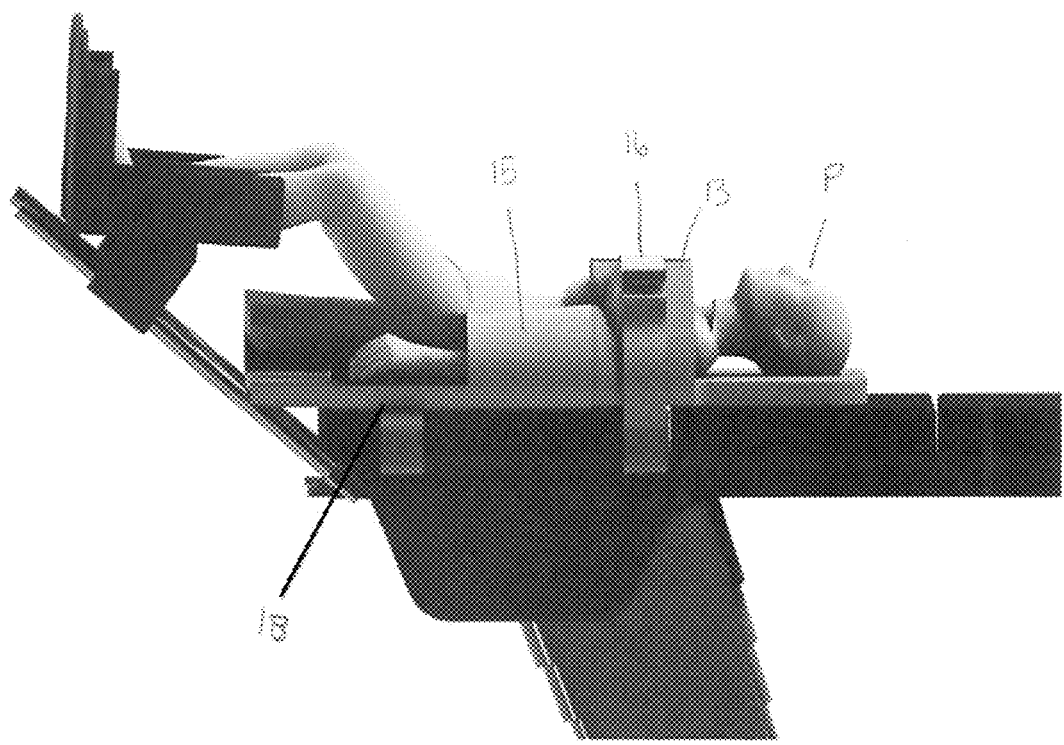
FIG. 9 is a side view of the same patient stabilization device showing the patient completely secured according to one embodiment of the present disclosure, with a cutout shown to illustrate that the foam extends beyond the patient's hands.
Figure 10:
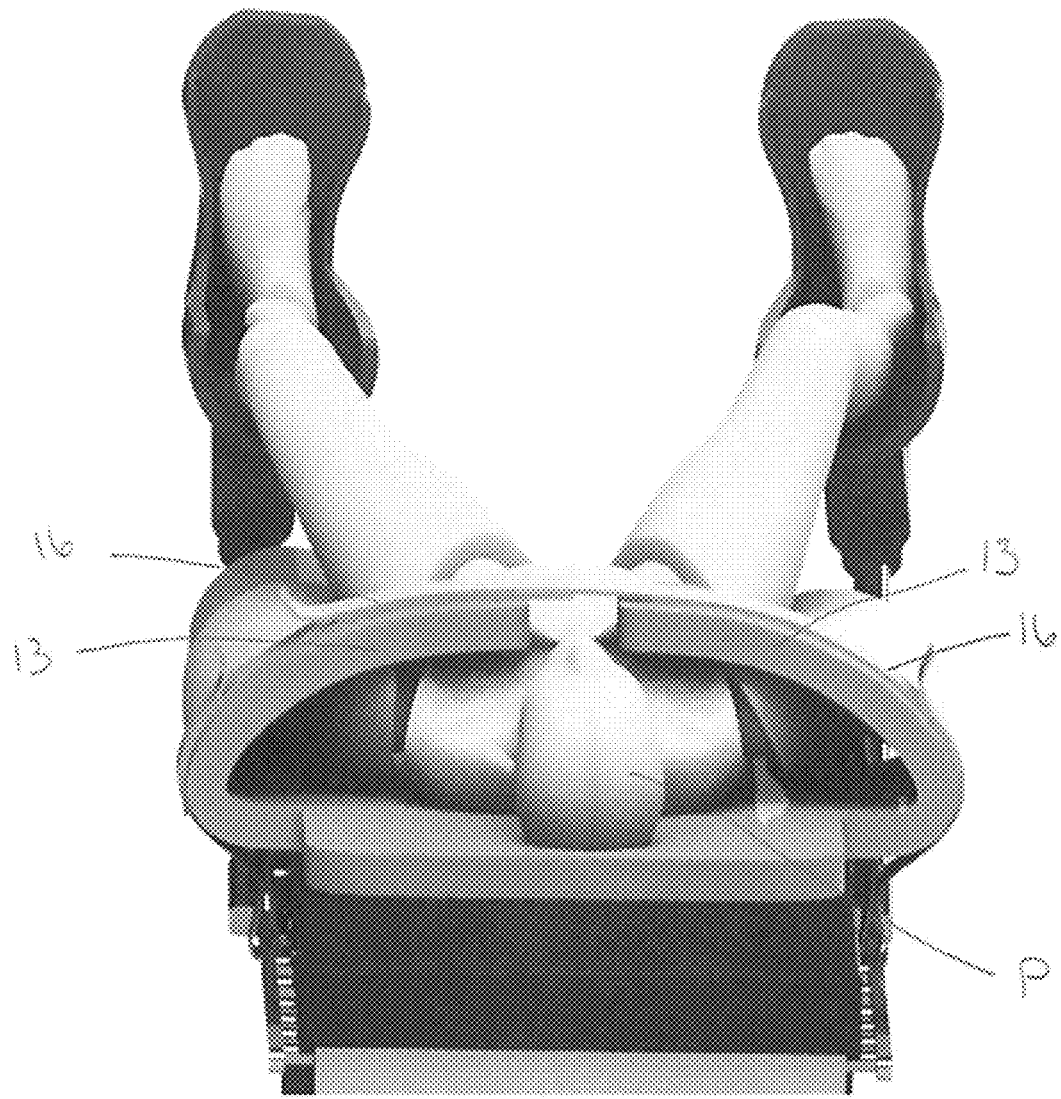
FIG. 10 is a front view of the same patient stabilization device showing the patient completely secured according to one embodiment of the present disclosure.
Figure 11:
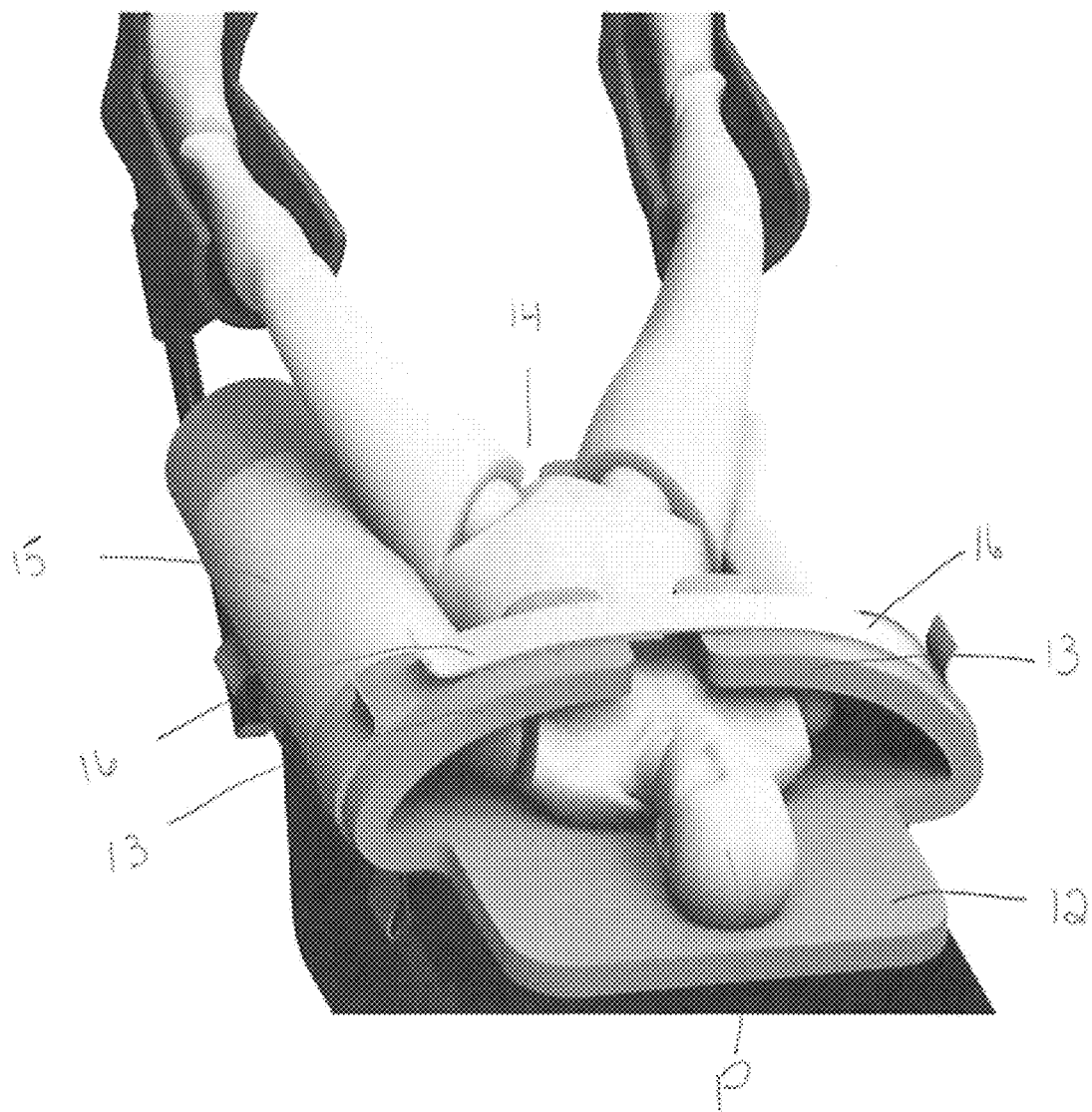
FIG. 11 is another front view of the same patient stabilization device showing the patient completely secured according to one embodiment of the present disclosure.
Figure 12:
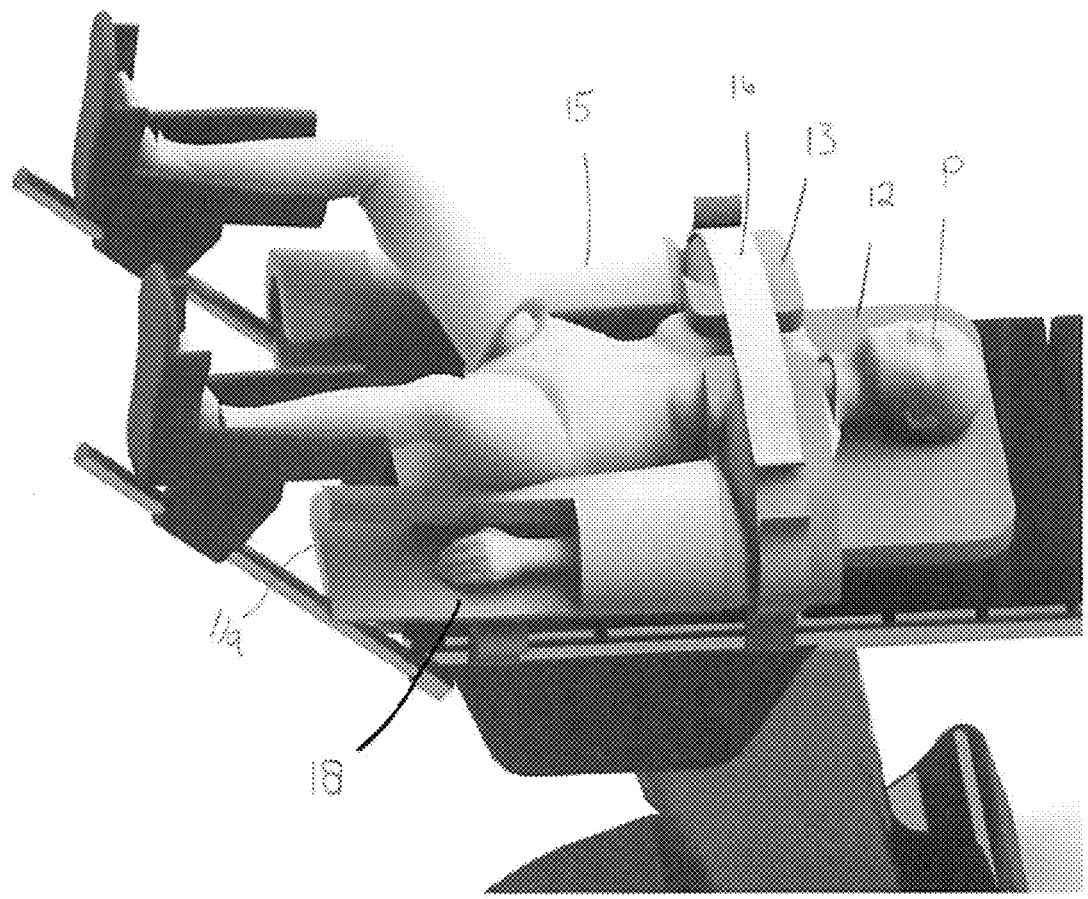
FIG. 12 is another side view of the same patient stabilization device showing the patient completely secured according to one embodiment of the present disclosure.
Figure 13:
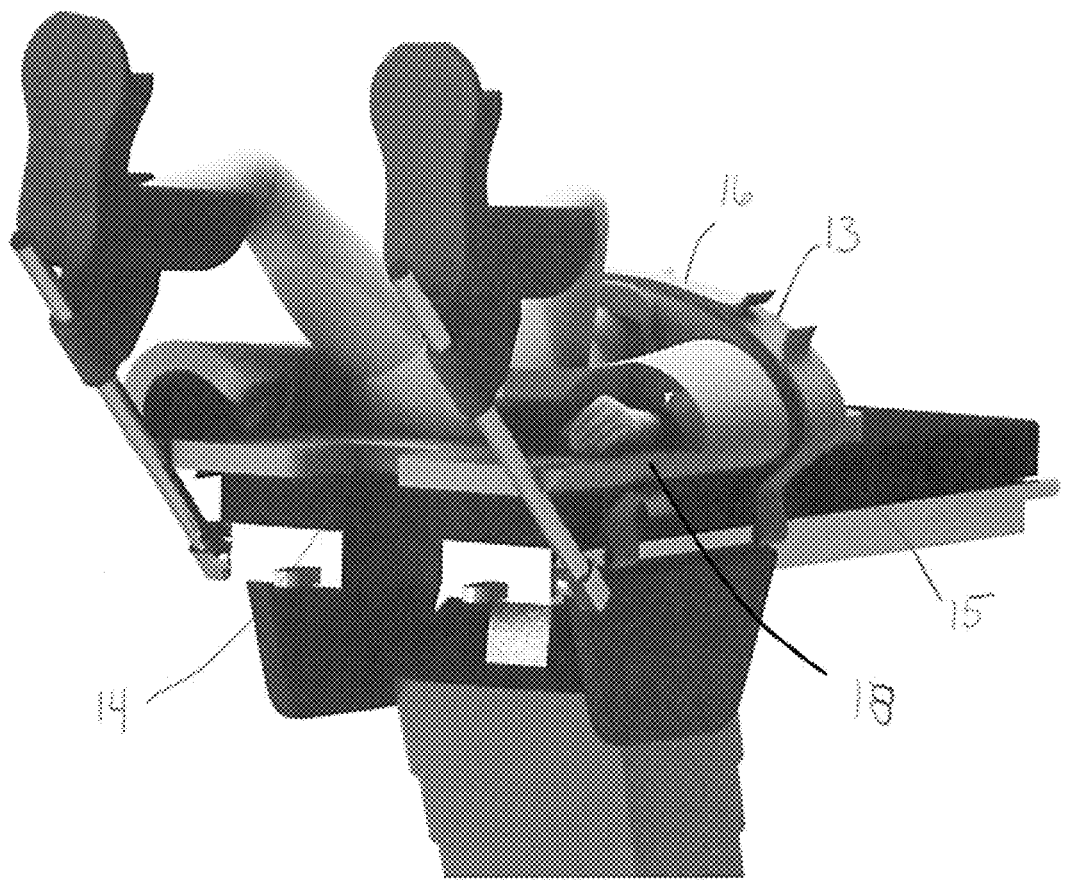
FIG. 13 is a inferior view of the same patient stabilization device showing the patient completely secured according to one embodiment of the present disclosure.
Figure 14:
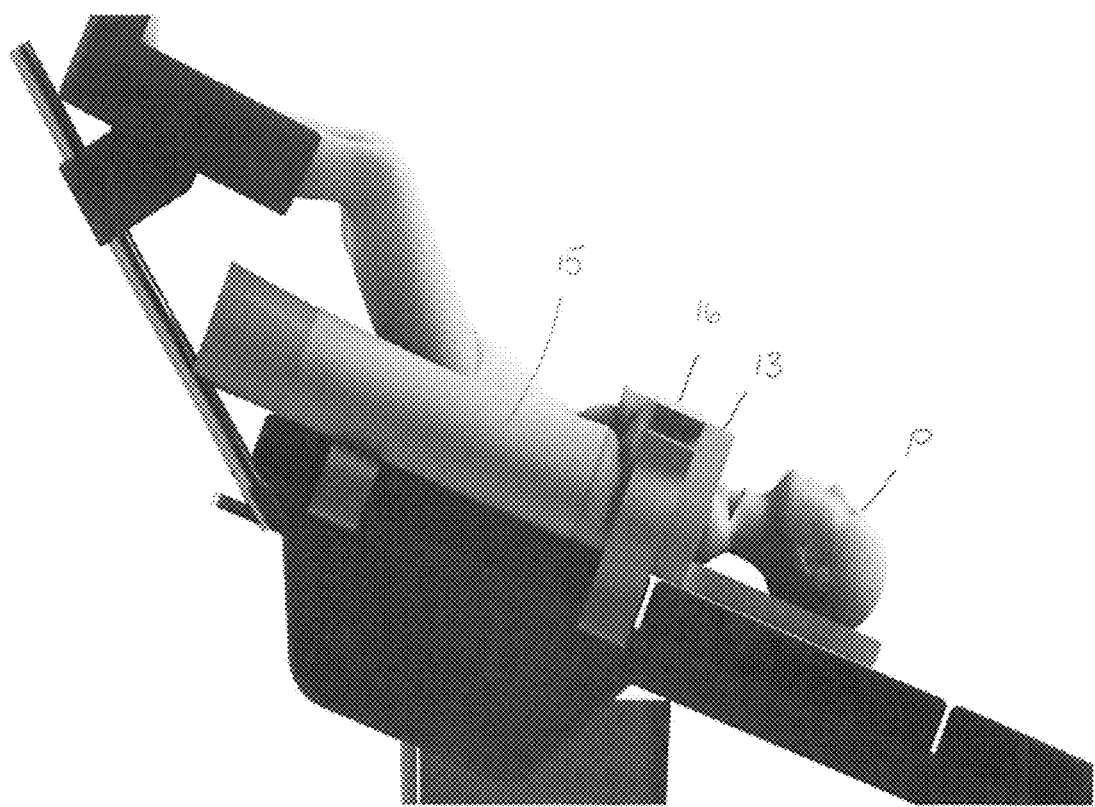
FIG. 14 is another side view of the same patient stabilization device showing the patient completely secured and in the Trendelenburg position according to one embodiment of the present disclosure.

FIGS. 8-14 are images from different angles showing a patient completely secured using the stabilizing device of the present disclosure. FIGS. 9, 12, and 13 show a cut-away section 18 highlighting how the patient's arms are securely wrapped in the device.

Figure 15:
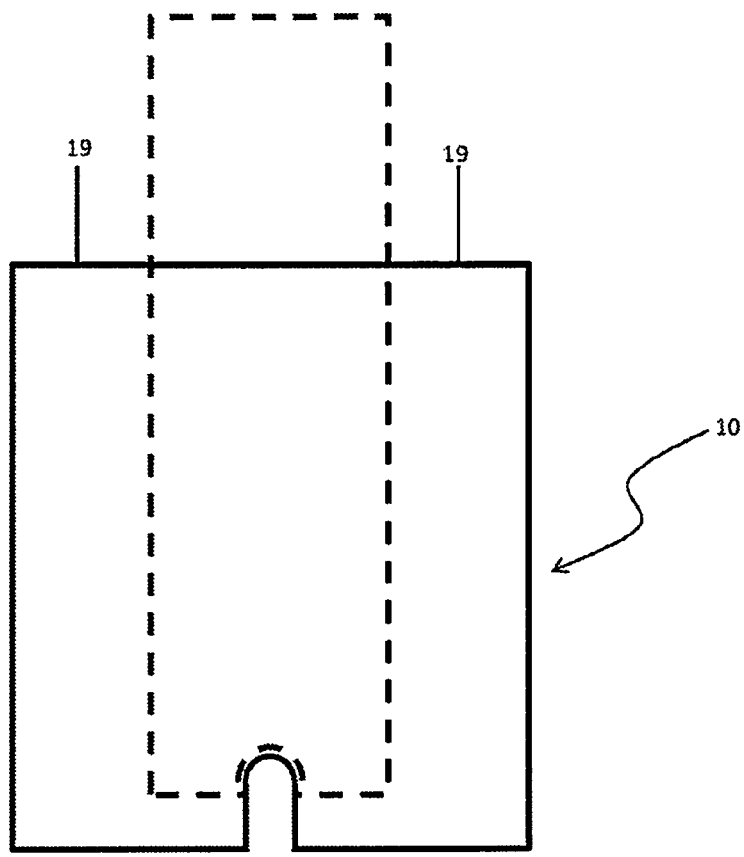
FIGS. 15-25 schematically show several different possible arrangements of a patient stabilization device.

FIG. 15 schematically shows a patient stabilization device 10 as viewed from above in relation to the outline of an OR table shown in dashed lines. The OR table is generally rectangular, but may have a perineal cutout that matches or partially matches the cutout notch in the device 10. As shown, the arm wings 19 extend laterally beyond the left and right edges of the OR table. The inferior edge of the device 10 is positioned so as to extend beyond the inferior edge of the table. Note that the device 10 by itself cannot generally support the entire weight of the patient, so that generally the patient's buttocks will be directly above the table while the patient's feet and legs are supported by stirrups. As shown in FIG. 15, the device has neither a head support portion nor chest wings.

Figure 16:
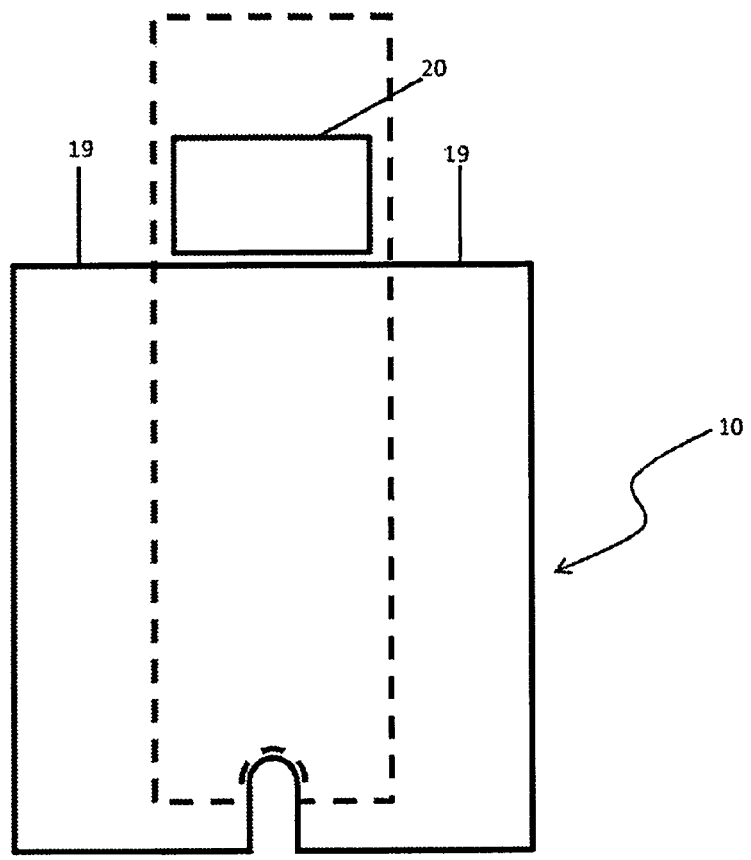

FIG. 16 shows the same device 10 with a detached head support portion 20. The head support 20 and device 10 can form a kit.

Figure 17:
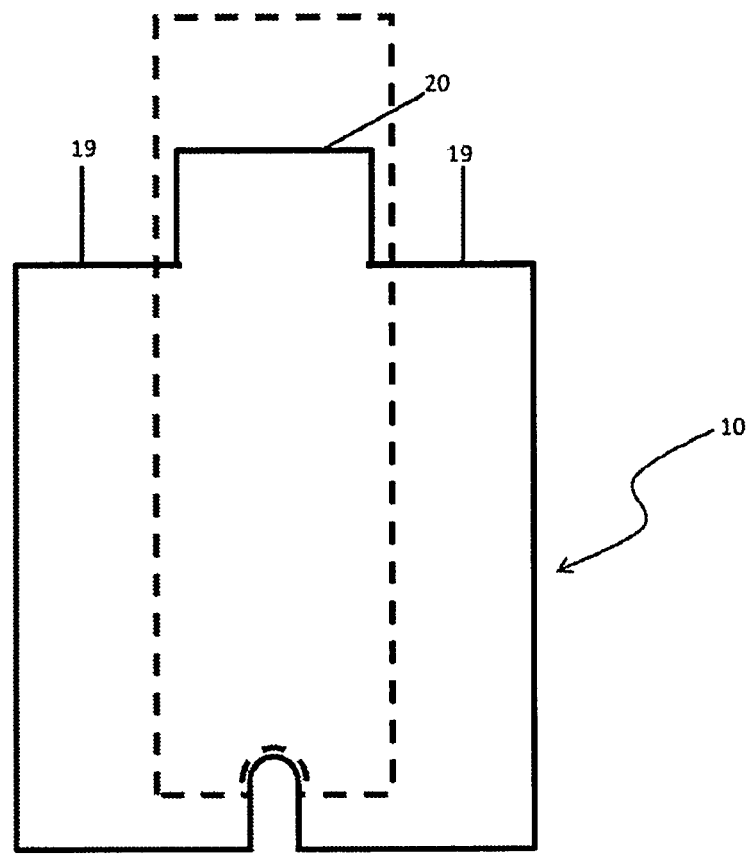

FIG. 17 shows a similar device 10 with an attached head support portion 20.

Figure 18:
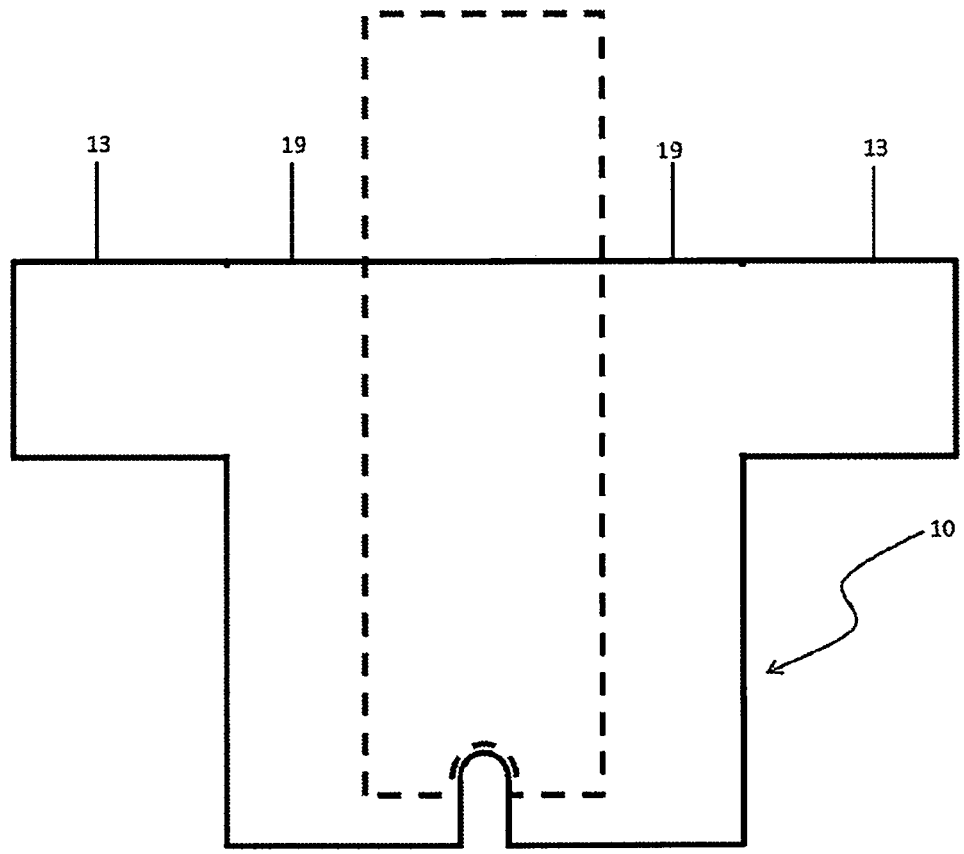

FIG. 18 shows a similar device 10 with side chest wings 13.

Figure 19:
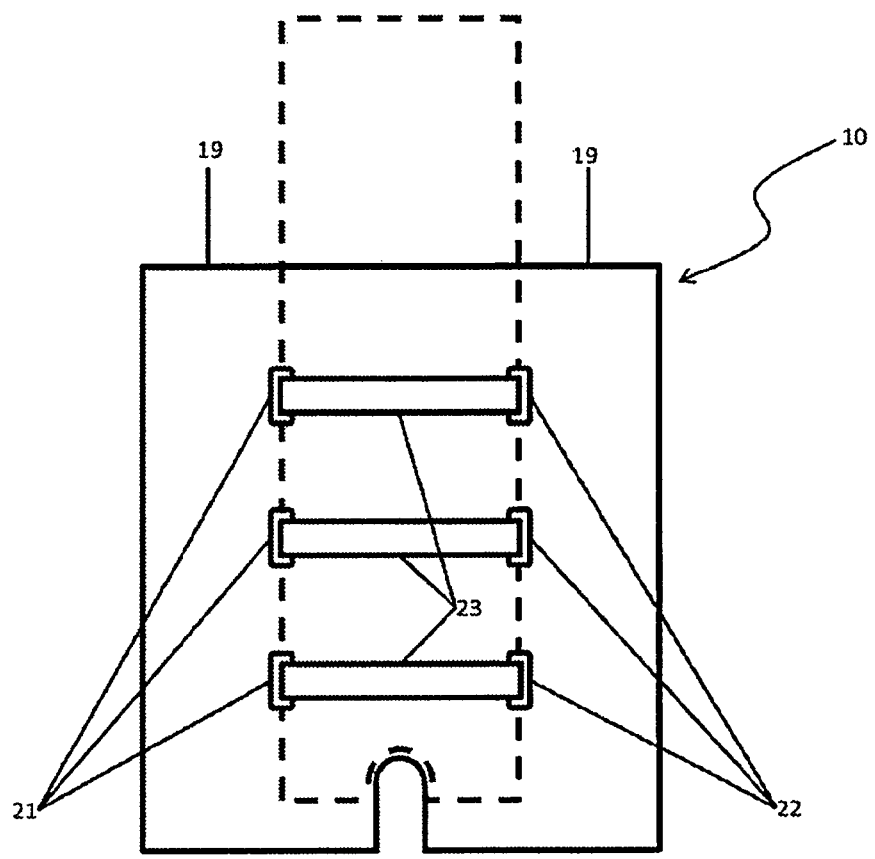

FIG. 19 shows a similar device 10 with through holes 21, 22. The holes can be used in conjunction with a fastener 23 to hold to device securely to the OR table. For example, a fastener 23 can be made of a single strap with fastening means, e.g., snaps, ties, hook and loop fastener, etc., at either end. The strap 23 can be positioned generally above the device but with either end extending through one of the holes 21, 22, and the fastening means fastened to the bed rails on the OR table. As shown, the device can accommodate up to three fasteners 23, each passing through a matched pair of holes. One fastener, or two fasteners may also be used.

Figure 20:
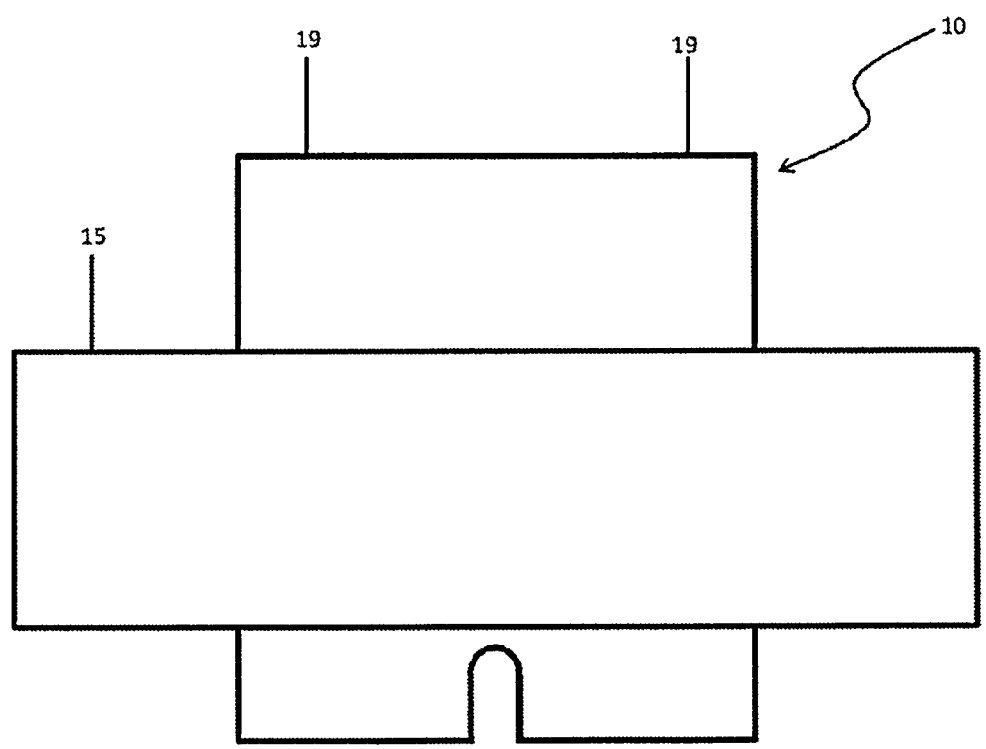
Figure 21:
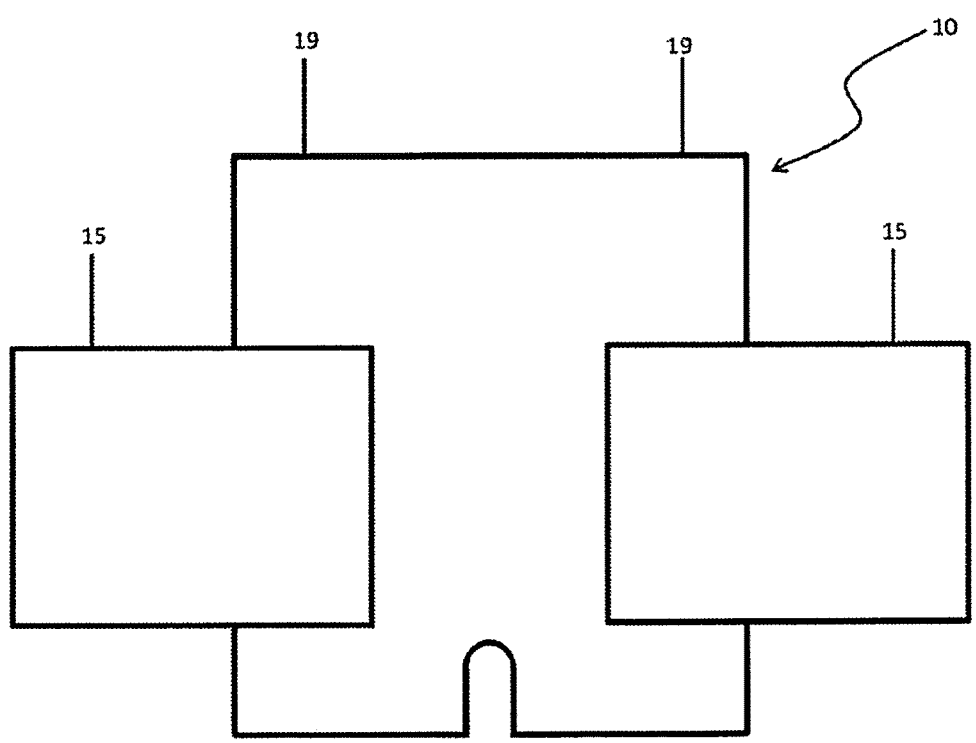

FIG. 20 shows a similar device 10 from the opposite side. As shown, the sheet 15 is made of a single integral piece affixed to the back, or bottom, of the device. FIG. 21 shows a similar device 10, except in this case the sheet 15 is made of two separate pieces each attached to the back of one of the two arm wings 19. As an alternative, the sheet or sheets could be attached to the front of the device. In that case, once the arm wings are rolled around the arms, the sheet would brought up between the arm and the torso, then pulled over the rolled-up arm, and tucked underneath the back of the device, or underneath an underlying mattress or mattress pad. This method would work to secure the arms using the weight of the patient, but has the drawback that it would typically not allow access to the bed rails or the underlying OR table for other attachments.

Figure 22:
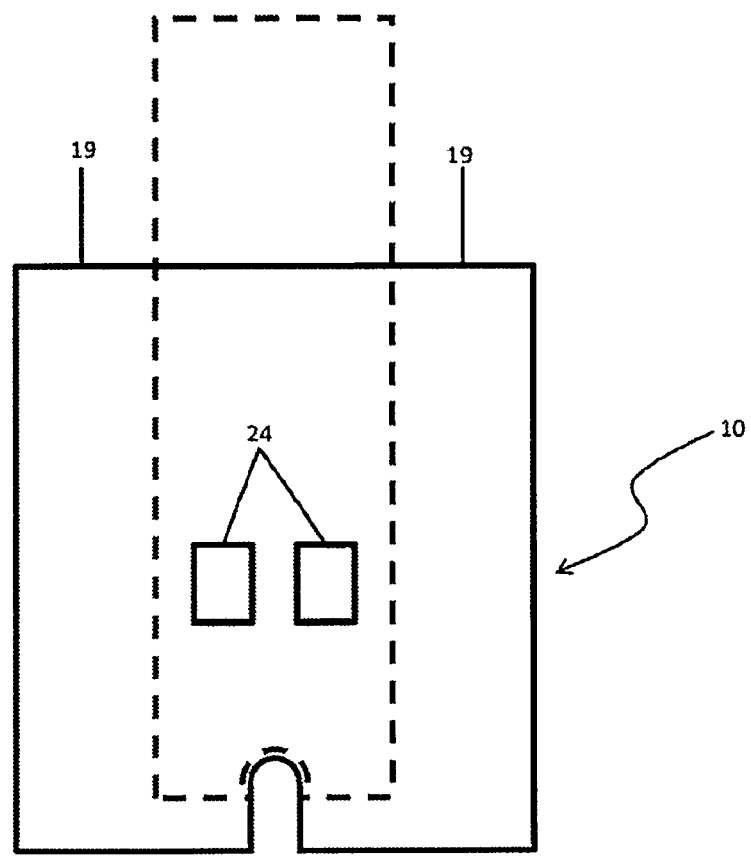

FIG. 22 shows a similar device 10 that also includes thermal elements 24. As shown, the device includes two thermal elements, but the device could include more or fewer. As shown, the thermal elements 24 are positioned to be roughly adjacent to the patient's kidneys, but may be positioned elsewhere.

There is preliminary work using thermography to differentiate between various anatomic structures such as blood vessels and ureters. However, a thermal gradient could be increased by increasing the temperature differential between a structure or structures of interest and the surrounding tissue or tissues.

Increasing the temperature (hyperthermia) or decreasing the temperature (hypothermia) of various organs is possible. The goal of this is generally to affect metabolic rate such as cooling a kidney to its reduce metabolic rate and prolong ischemia time and to improve outcomes during renal transplantation. Such cooling requires placing the organ that has been exteriorized or placing a cooling instrument or mechanism into the patient or body cavity.

This invention is designed to thermoregulate tissues or organs such as the kidney, through a transcutaneous approach with the goal in cooling or warming the urine or renal vasculature compared to body temperature in an attempt to utilize the temperature gradient created by this minimally invasive approach and to enhance the thermography gradient and improve the detection, identification, localization and resolution of the ureter or renal blood vessels during surgery through an open (laparotomy), laparoscopy and other procedures that would benefit from the correct identification of the ureter.

Such a cooling or heating device could be integrated into a patient wrap, stabilizing pad, foam or similar device or be integrated into an operating and procedure table.

In order to change the temperature of the kidney for instance, a device would be placed on the skin. For instance, the device would be placed on the back or side of the patient, adjustable to the general location of the kidneys if the kidneys were the desired organ to thermoregulate. This device could employ a variety of heating and cooling elements that including but not limited to cooling fluid, ice, cold gas, warming fluid, warm gas, warming elements vibratory elements. Other devices that can transmit heat or cold transcutaneously could also be used. In an attempt to avoid increasing or decreasing the patient's overall body temperature, an additional device with fluid or gas that warms if the main device cools and cools if the main device warms may be used. This could serve two purposes, to maintain overall patient thermoregulation and also to further increase the temperature gradient. For instance, a warming pad could be placed along the patients back to warm the posterior surface of the patient and retroperitoneal structures while at the same time cooling the kidney and urine so that when the urine flows inside the ureter, along the retroperitoneum, it would be easier to differentiate from the adjacent tissue.

This external (transcutaneous) regulation of temperature is not limited to the kidney and could be utilized to identify other tissues or structures such as vascular and neural structure both benign and malignant as it may be possible that malignant and benign tissues have a different propensity to absorb heat or cold.

Figure 23:
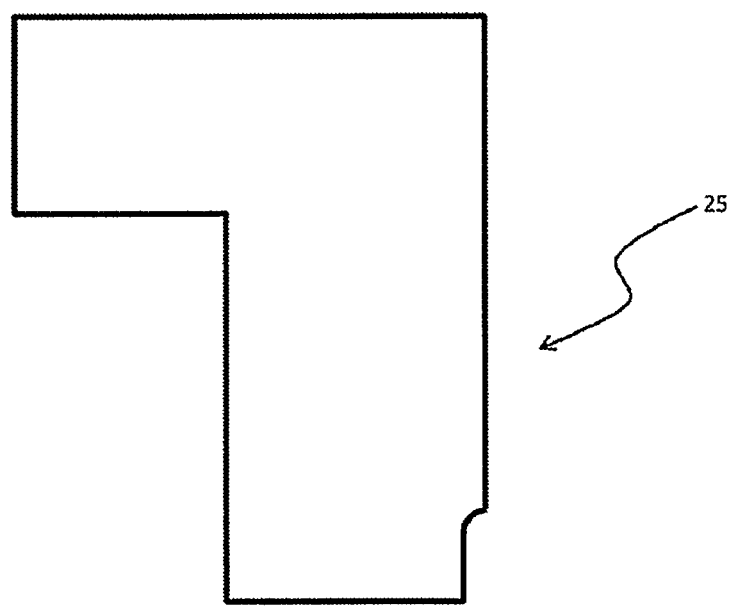

FIG. 23 shows a portion 25 of a similar device. As shown, the portion is one half of one embodiment of a stabilization device. An entire stabilization device may be assembled from two such parts 25 that are mirror-images of one another, but otherwise identical. This method of construction can be efficient, particularly when cutting the parts 25 from sheets of support material of a preset size. Alternatively, the entire support portion of the device can be integrally constructed from a single piece. As another alternative, the support portion may be constructed out of differently sized and shaped pieces.

One benefit of the sort of device shown in the figures is that the patient is wrapped in, and held in place with, parts having a large extent, both laterally and in the inferior-superior directions. By wrapping the patient with large lengths of the support material, either on the arm wings or the chest wings, or both, the friction force necessary to hold the patient in place is generated over a large area, reducing the possibility of concentrated pressure points that could result in nerve injury. The uniformity of the pressure on the patient is more comfortable, and more safe.

Figure 24:
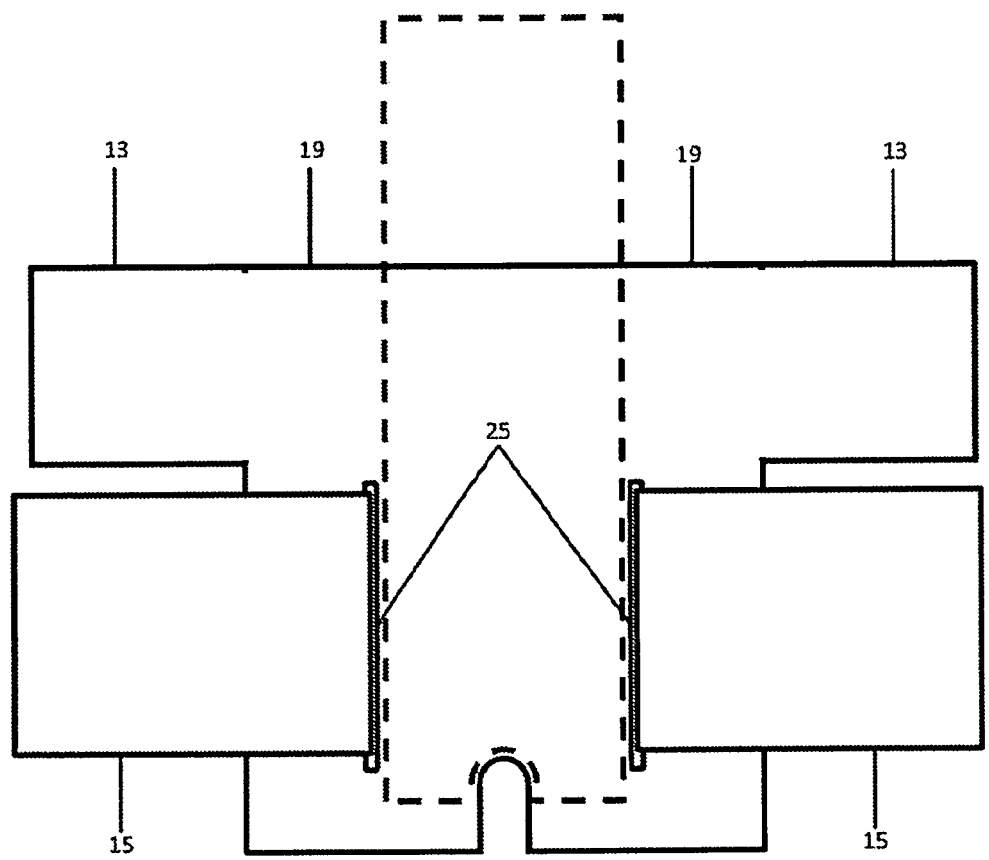
Figure 25:
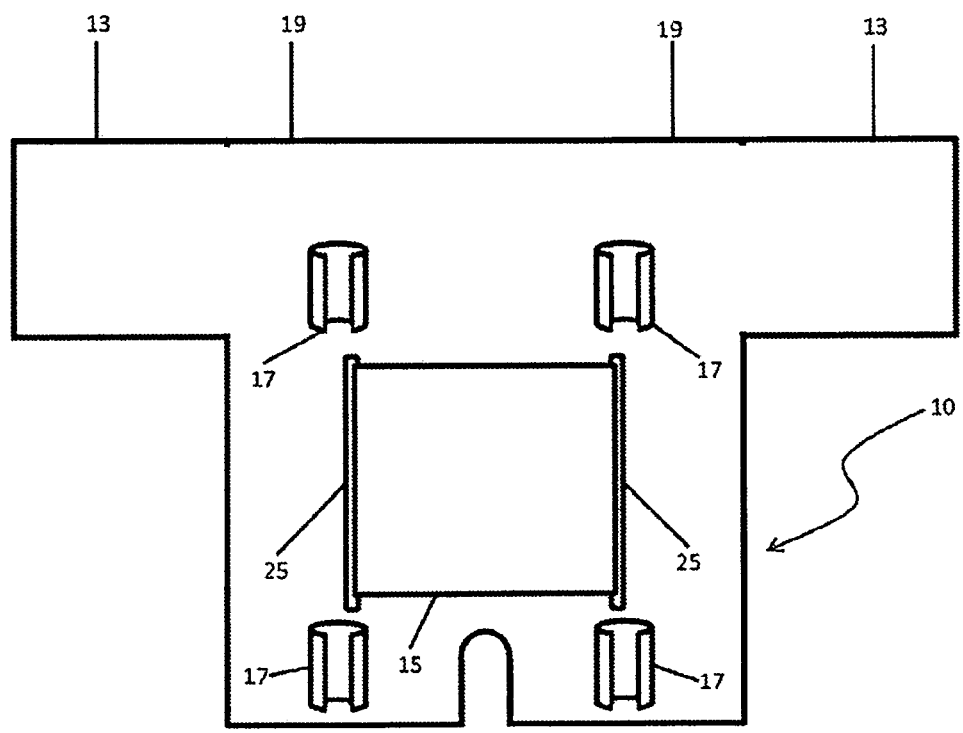

FIG. 24 schematically shows yet another alternative device viewed from above. In this case, the sheets 15 are positioned through two long slots 25 through the device. The slots 25 are positioned so that, when the patient is positioned on the device, the slots 25 are between the patient's arms and torso. The sheets 15 can then be raised vertically between the arm and torso. The arm wings 19 can be wrapped around the patient's arms, and the sheets 15 can be wrapped around the wrapped arm wings 19 in the opposite direction, down around the outside of the arm, and beneath the device. The sheets 15 can then be held in place either by tucking them under the device and using the weight of the patient, or by some fastening means, such as snaps, buttons, ties, straps, hook and loop fasteners, etc. FIG. 25 shows the same device as FIG. 24 viewed from below. In this case, the sheet 15 is a single piece, but can alternatively be two separate sheets. Because the slots 25 are between the OR table rails, the device can be attached with fasteners 17 similar to those shown in FIG. 4 more readily than with the fasteners of FIG. 19.

Summary of Certain Embodiments

A device can be used for stabilizing a human patient on an operating table, the operating table having a width and a length. The device can include a generally planar support, a left and a right arm sheet, an immobilizing fastener configured to secure the support to the operating table. The generally planar support can have a body portion and on either side of the body portion a left arm wing and a right arm wing, the support having opposed superior and inferior edges, opposed left and right lateral edges and an opposed top and bottom. The body portion can extend from the superior edge to the inferior edge, the inferior edge defining a notch indented into the body portion. The left and right arm wings and can extend along the left and right lateral edges respectively. The body portion can have a lateral width about equal to the width of the operating table. The support can have a lateral width greater than the width of the operating table. The support can be sized and shaped such that when the support is laid flat with its bottom on the operating table and the patient is supine on the body portion, then the patient's left and right arms rest on the left and right arm wings respectively. The support can also be sized and shaped such that when the support is laid flat with its bottom on the operating table, the patient is supine on the body portion, and the patient's shoulders are aligned with the superior edge of the body portion, then the patient's perineum is positioned near, at, adjacent to, or above the notch and the patient's hands lie superior to the inferior edge. The left and right arm sheets can be fixedly attached to the bottom of the left and right arm wings respectively, and the left and right arm sheets can extend laterally beyond the left and right lateral edges respectively.

In some such devices, the support is constructed entirely of a single material. In some such devices the support includes convoluted polyurethane foam. In some such devices the support is integrally constructed of a single piece of material, while in others the support is constructed of a plurality of pieces, for example, the plurality of pieces can be two pieces having mirror symmetry, or a piece corresponding to the body portion, a piece corresponding to the left arm wing, and a piece corresponding to the right arm wing are can be among the plurality of pieces.

Some such devices can also include an infection control sheet fixedly attached to the bottom of the body portion adjacent to the inferior edge so as to at least partially cover the notch.

In some such devices the left and right arm sheets are parts of a single sheet. In some such devices the left and right arm sheets each do not include any fastener.

Some such devices can also include left and right support structures fixedly attached to the bottoms of the left and right arm wings respectively, the left and right support structures offering substantially no resistance to folding the left and right arm wings respectively toward the top, but offering resistance to folding the left and right arm wings respectively toward the bottom. The resistance can be sufficient to support the weight of a human arm.

Some such devices can also include left and right chest wings extending from the left and right lateral edges respectively, the left and right chest wings each having a superior edge contiguous with the superior edge of the support. In such devices, the left and right chest wings can include left and right chest fasteners respectively, the left and right chest fasteners being configured fasten to each other when the left and right chest wings are folded over the chest of a patient supine on the body portion. The left and right chest fasteners can be hook and loop fasteners.

In some such devices, the body can define two through-holes each sized, shaped and located to align with a fixation element of the table, for example, a bed rail, and the immobilizing fastener can include a strap, a first hook and loop fastener at one end of the strap and a second hook and loop fastener at the opposite end of the strap, the strap disposed to pass through both through-holes. Similarly, the body can define four such through-holes with two such straps disposed through the through-holes. Similarly, the body can define six such through-holes with three such straps disposed through the through-holes.

Some such devices also include a thermal element configured to alter the temperature of at least a portion of the patient when the thermal element is brought into thermal contact with the patient. In such devices, the body portion can define a thermal element retainer and the thermal element can be securely retained in the thermal element retainer. The thermal element retainer can be a pocket, for example a sealable pocket, and/or may be formed by a void or cutout in the body portion. The thermal element can be a heating element or a cooling element. The thermal element may be passive, such as an pack containing compounds undergoing endothermic or exothermic reaction, or the heating element may be actively controlled, as by a thermostatic circuit. The thermal element can be located on the device such that, when the patient is supine on the body portion, and the patient's shoulders are aligned with the superior edge of the body portion, then the thermal element is aligned with a kidney and/or a ureter of the patient.

Some such devices also include a head support attached to and extending from extending from the superior edge of the body portion. Some such devices are included in kits that also include a head portion configured to support the head of the patient when the head support is placed adjacent to the superior edge of the body portion.

A patient can be stabilized on an operating table using a stabilization device, the patient having left and right arms, shoulders, a torso, a back, and a perineum, by: affixing the device to the operating table by securing the immobilizing fastener to the operating table with the device laid flat with its bottom on the operating table; laying the patient on the device such that the patient is supine, the patient's arms rest by the patient's side on the left and right arm wings, and the patient's torso rests on the body portion with the patient's shoulder's aligned with the superior edge of the body portion, so that the patient's perineum rests above the notch and the patients hands lie superior to the inferior edge; wrapping the left and right arm wings around the left and right arms respective of the patient; wrapping the left arm sheet over the left arm, down between the left arm and the patient's torso, and tucking the left arm sheet beneath the patient's back so that the patient is lying on top of a portion of the left arm sheet; and wrapping the right arm sheet over the right arm, down between the right arm and the patient's torso, and tucking the right arm sheet beneath the patient's back so that the patient is lying on top of a portion of the right arm sheet.

Where the device includes a thermal element, such methods can also include positioning a first predetermined portion of the patient adjacent to the thermal element; heating or cooling the first predetermined portion relative to the rest of the patient; visualizing the first predetermined portion and/or a second predetermined portion of the patient in fluid communication with the predetermined portion by detecting thermal variation of the first and/or second predetermined portions with respect to the rest of the patient.

Such methods can also be accomplished by similarly using the kit described above.

A device for stabilizing a patient can include a body portion, a thermal element, and a thermal element retainer. The body portion can be sized and shaped to support at least a supported portion of the patient's body. The thermal element can be securely retained to the body portion by the thermal element retainer. The thermal element can be configured to alter the temperature of at least a first predetermined portion of the supported portion of the patient when the thermal element is brought into thermal contact with the patient. The thermal element can be positioned relative to the body portion such that, when the supported portion is supported by the body portion, the thermal element is positioned adjacent to and in thermal contact with the first predetermined portion. The thermal element retainer can be a sealable pocket. The thermal element can be a heating element or a cooling element. The thermal element may be passive, such as an pack containing compounds undergoing endothermic or exothermic reaction, or the heating element may be actively controlled, as by a thermostatic circuit. The supported portion can include a torso of the patient, and the first predetermined portion of the patient can include a kidney and/or a ureter of the patient.

Such a device can be used in immobilizing a patient in any of the ways described above. Such methods of immobilizing a patient can include visualizing the first predetermined portion of the patient and/or a second predetermined portion of the patient in fluid communication with the first predetermined portion by detecting thermal variation of the first and/or second predetermined portions with respect to the rest of the patient. The visualizing can include, for example, optical or infrared imaging of the first and/or second predetermined portions. The first predetermined portion can be a kidney of the patient, and the second predetermined portion can be a ureter of the patient.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosures described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The invention claimed is:

1. A device for stabilizing a human patient on an operating table, the operating table having a width and a length, the device comprising:
    a generally planar support having a body portion and on either side of the body portion a left arm wing and a right arm wing, the support having opposed superior and inferior edges, opposed left and right lateral edges and an opposed top and bottom;
    wherein:
        the body portion having an upper surface and an opposed bottom surface defining a thickness therebetween, the body portion extends from the superior edge to the inferior edge to define a length therebetween, wherein the body portion length is greater than the length of the operating room table with the inferior edge of the body portion extending beyond the inferior edge of the operating table, the inferior edge defining a notch indented into the body portion, the notch extending a first length toward the superior edge and a second length toward the lateral edges and coextensively in the top and bottom surfaces throughout the entire thickness of the body portion, the first length greater than the second length;
        the left and right arm wings extend along the left and right lateral edges of the body portion to define a length such that the inferior edge of the left and right arm wings extend beyond the inferior edge of the operating table, the inferior edge of the arm wings aligned with the inferior edge of the body portion;
        the body portion has a lateral width substantially equal to the width of the operating table;
        the support has a lateral width greater than the width of the operating table;
    the device further comprising a left and a right arm sheet fixedly attached to the bottom of the left and right arm wings respectively, the left and right arm sheets extending laterally beyond the left and right lateral edges respectively and configured to wrap around the hands of the patient; and
    an immobilizing fastener configured to secure the support to the operating table.

2. The device of claim 1 wherein the device further comprises a thermal element configured to alter the temperature of at least a portion of the patient when the thermal element is brought into thermal contact with the patient.

3. The device of claim 2 wherein the body portion defines a thermal element retainer and the thermal element is securely retained in the thermal element retainer.

4. The device of claim 3 wherein the thermal element retainer is a sealable pocket.

5. The device of claim 2 wherein the thermal element is a cooling element.

6. The device of claim 2 wherein the thermal element is a heating element.

7. The device of claim 2 wherein the thermal element is located on the device at a position spaced from the edges of the device.

8. The device of claim 1 further comprising left and right chest wings extending from the left and right lateral edges respectively, the left and right chest wings each having a superior edge contiguous with the superior edge of the support, the left and right arm sheets extending laterally beyond the lateral edges of the left and right chest wings.

9. The device of claim 8 wherein the left and right chest wings include left and right chest fasteners respectively, the left and right chest fasteners being configured to fasten to each other when the left and right chest wings are folded over.

10. The device of claim 9 wherein the left and right chest fasteners are hook and loop fasteners.

11. The device of claim 1 wherein the support is constructed of a plurality of pieces.

12. The device of claim 11 wherein the plurality of pieces are two pieces having mirror symmetry.

13. The device of claim 11 wherein a piece corresponding to the body portion, a piece corresponding to the left arm wing, and a piece corresponding to the right arm wing are among the plurality of pieces.

14. A kit comprising:
the device of claim 1; and
a head support configured to support the head of the patient when the head support is placed adjacent to the superior edge of the body portion.

15. A method of stabilizing a patient on an operating table using the kit of claim 14, the patient having left and right arms, shoulders, a head, a torso, a back, and a perineum, the method comprising:
affixing the device of claim 1 to the operating table by securing the immobilizing fastener to the operating table with the device laid flat with its bottom on the operating table;
placing the head support on the operating table adjacent to the superior edge of the body portion;
laying the patient on the device such that the patient is supine, the patient's arms rest by the patient's side on the left and right arm wings, the patient's head rests on the head portion, and the patient's torso rests on the body portion with the patient's shoulder's aligned with the superior edge of the body portion, so that the patient's perineum rests above the notch and the patients hands lie superior to the inferior edge;
wrapping the left and right arm wings around the left and right arms respective of the patient;
wrapping the left arm sheet over the left arm, down between the left arm and the patient's torso, and tucking the left arm sheet beneath the patient's back so that the patient is lying on top of a portion of the left arm sheet; and
wrapping the right arm sheet over the right arm, down between the right arm and the patient's torso, and tucking the right arm sheet beneath the patient's back so that the patient is lying on top of a portion of the right arm sheet.

16. A method of stabilizing a patient on an operating table using the device of claim 1, the patient having left and right arms, shoulders, a torso, a back, and a perineum, the method comprising:
affixing the device to the operating table by securing the immobilizing fastener to the operating table with the device laid flat with its bottom on the operating table;
laying the patient on the device such that the patient is supine, the patient's arms rest by the patient's side on the left and right arm wings, and the patient's torso rests on the body portion with the patient's shoulder's aligned with the superior edge of the body portion, so that the patient's perineum rests above the notch and the patients hands lie superior to the inferior edge;
wrapping the left and right arm wings around the left and right arms respective of the patient;
wrapping the left arm sheet over the left arm, down between the left arm and the patient's torso, and tucking the left arm sheet beneath the patient's back so that the patient is lying on top of a portion of the left arm sheet; and
wrapping the right arm sheet over the right arm, down between the right arm and the patient's torso, and tucking the right arm sheet beneath the patient's back so that the patient is lying on top of a portion of the right arm sheet.

17. The method of claim 16 further comprising:
positioning a first predetermined portion of the patient adjacent to the thermal element;
heating or cooling the first predetermined portion relative to the rest of the patient;
visualizing the first predetermined portion and/or a second predetermined portion of the patient in fluid communication with the first predetermined portion by detecting thermal variation of the first and/or second predetermined portions with respect to the rest of the patient.

18. The device of claim 1 wherein the support is constructed entirely of a single material.

19. The device of claim 1 wherein the support comprises convoluted polyurethane foam.

20. The device of claim 1 wherein the support is integrally constructed of a single piece of material.

21. The device of claim 1 further comprising an infection control sheet fixedly attached to the bottom of the body portion adjacent to the inferior edge so as to at least partially cover the notch.

22. The device of claim 1 wherein the left and right arm sheets are parts of a single sheet.

23. The device of claim 1 wherein the left and right arm sheets each do not comprise a fastener.

24. The device of claim 1 further comprising left and right support structures fixedly attached to the bottoms of the left and right arm wings respectively, the left and right support structures offering substantially no resistance to folding the left and right arm wings respectively toward the top, but offering resistance to folding the left and right arm wings respectively toward the bottom.

25. The device of claim 1 wherein:
the body portion defines two through-holes each sized, shaped and located to align with a fixation element of the table; and
the immobilizing fastener comprises a strap, a first hook and loop fastener at one end of the strap and a second hook and loop fastener at the opposite end of the strap, the strap disposed to pass through both through-holes.

26. The device of claim 1 wherein:
the body portion defines four through-holes each sized, shaped and located to align with a fixation element of the table; and
the immobilizing fastener comprises two straps, a first hook and loop fastener at one end of each strap and a second hook and loop fastener at the opposite end of each strap, each strap disposed to pass through two through-holes, so that a single strap passes through each through hole.

27. The device of claim 1 wherein:
the body portion defines six through-holes each sized, shaped and located to align with a fixation element of the table; and
the immobilizing fastener comprises three straps, a first hook and loop fastener at one end of each strap and a second hook and loop fastener at the opposite end of each strap, each strap disposed to pass through two through-holes, so that a single strap passes through each through hole.

28. The device of claim 1 wherein the planar support further comprises a head support attached to and extending from the superior edge.

29. The device of claim 1 wherein the support comprises polyurethane, silicone, vinyl, nylon, or polyethylene vinyl acetate (PEVA).

30. The device of claim 1, wherein the fastener is fixedly attached to the bottom side of the device.

31. The device of claim 1, wherein the bottom side of the support further comprises a slip-resistant material.

32. The device of claim 1, wherein the notch is configured in a generally U-shape having two sides extending beyond the inferior edge of the operating room table.

33. The device of claim 1, wherein the left and right arm sheets are attached to the bottom surface of the device, with the arm wings configured to fold over from a first generally planar position, to a second arcuate position wherein a top surface of the arm sheet is in contact with a top surface of the body portion.

* * * * *